United States Patent
Choi et al.

(10) Patent No.: US 11,466,001 B2
(45) Date of Patent: Oct. 11, 2022

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Yeong Suk Choi, Suwon-si (KR); Ji Soo Shin, Seoul (KR); Chul Baik, Suwon-si (KR); Sung Young Yun, Suwon-si (KR); Taejin Choi, Suwon-si (KR); Hye Rim Hong, Suwon-si (KR); Kyung Bae Park, Hwaseong-si (KR); Gae Hwang Lee, Seongnam-si (KR); Chul Joon Heo, Busan (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 275 days.

(21) Appl. No.: 16/835,934

(22) Filed: Mar. 31, 2020

(65) Prior Publication Data
US 2020/0308167 A1    Oct. 1, 2020

(30) Foreign Application Priority Data
Apr. 1, 2019    (KR) ........................ 10-2019-0038059

(51) Int. Cl.
*H01L 29/08*    (2006.01)
*C07D 421/14*    (2006.01)
(Continued)

(52) U.S. Cl.
CPC .......... *C07D 421/14* (2013.01); *C07F 7/0816* (2013.01); *C07F 7/30* (2013.01);
(Continued)

(58) Field of Classification Search
CPC .............. H01L 27/307; H01L 51/0072; H01L 51/0074; H01L 51/0094; H01L 51/42; C07F 7/0816; C07F 7/30
(Continued)

(56) References Cited

U.S. PATENT DOCUMENTS

| 8,525,577 B2 | 9/2013 | Yofu et al. |
| 9,252,369 B2 | 2/2016 | Anemian et al. |

(Continued)

FOREIGN PATENT DOCUMENTS

| JP | 4760559 B2 | 8/2011 |
| JP | 2014237682 A | 12/2014 |

(Continued)

OTHER PUBLICATIONS

H. Seo et al., 'Color Sensors with Three Vertically Stacked Organic Photodetectors' *Japanese Journal of Applied Physics*, vol. 46, No. 49, 2007, pp. L1240-L1242.
(Continued)

*Primary Examiner* — Phuc T Dang
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:
(Continued)

[Chemical Formula 1]

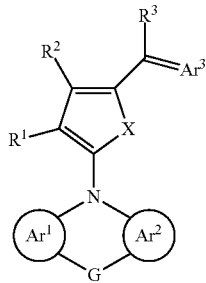

In Chemical Formula 1, each substituent is the same as defined in the detailed description.

31 Claims, 9 Drawing Sheets

(51) Int. Cl.
    *H01L 27/30*     (2006.01)
    *H01L 51/42*     (2006.01)
    *C07F 7/08*     (2006.01)
    *H01L 51/00*     (2006.01)
    *C07F 7/30*     (2006.01)

(52) U.S. Cl.
    CPC ........ *H01L 27/307* (2013.01); *H01L 51/0072* (2013.01); *H01L 51/0074* (2013.01); *H01L 51/0094* (2013.01); *H01L 51/42* (2013.01)

(58) Field of Classification Search
    USPC .......................................... 257/40
    See application file for complete search history.

(56) References Cited

U.S. PATENT DOCUMENTS

| | | | |
|---|---|---|---|
| 9,941,477 B2 | 4/2018 | Choi et al. | |
| 10,396,295 B2 | 8/2019 | Numata et al. | |
| 10,490,747 B2 | 11/2019 | Anemian et al. | |
| 2010/0032658 A1 | 2/2010 | Lee et al. | |
| 2015/0255723 A1* | 9/2015 | Kim | H01L 51/504 |
| | | | 549/382 |
| 2017/0077405 A1 | 3/2017 | Lim et al. | |
| 2017/0110671 A1* | 4/2017 | Lee | H01L 51/0052 |
| 2017/0148994 A1* | 5/2017 | Choi | H01L 51/525 |
| 2017/0179400 A1* | 6/2017 | Hwang | C09K 11/025 |
| 2017/0271611 A1 | 9/2017 | Li et al. | |
| 2019/0169139 A1 | 6/2019 | Franz et al. | |

FOREIGN PATENT DOCUMENTS

| | | |
|---|---|---|
| KR | 20130036335 A | 4/2013 |
| KR | 20140043951 A | 4/2014 |
| KR | 20150110363 A | 10/2015 |
| KR | 20170060488 A | 6/2017 |
| KR | 20170104008 A | 9/2017 |
| KR | 20180032354 A | 3/2018 |
| WO | WO-2016029137 A1 | 2/2016 |

OTHER PUBLICATIONS

S. Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

M. Ihama et al., 'CMOS Image Sensor with a Thin Overlaid Panchromatic Organic Photoconductive Layer for Sensors with Reduced Pixel Size' *IDW* 2009, pp. 2123-2126.

Y. Pihosh et al. "Photocatalytic generation of hydrogen by core-shell $WO_3/BiVO_4$ nanorods with ultimate water splitting efficiency" Scientific Reports, 5:11141, Jun. 8, 2015.

Seon-Jeong Lim et al., 'Organic-on-silion complementary metal-oxide-semiconductor colour image sensors' *Scientific Reports*, 5:7708, Jan. 2015.

Juha Alakarhu, 'Image Sensors and Image Quality in Mobile Phones' printed in the outline of 2007 International Image Sensor Workshop (Ogunquit Maine, USA).

Kazuko Takahashi et al., 'Efficient Synthesis of 2-IODO and 2-Dicyanomethyl Derivitives of Thiophene, Selenophene, Tellurophene, and Thieno[3,2-b]Thiophene' *Heterocycles*, vol. 43, No. 9, 1996, pp. 1927-1935.

* cited by examiner

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority to and the benefit of Korean Patent Application No. 10-2019-0038059 filed in the Korean Intellectual Property Office on Apr. 1, 2019, the entire contents of which are incorporated herein by reference.

BACKGROUND

1. Field

Example embodiments provide a compound and a photoelectric device, an image sensor, and an electronic device including the same.

2. Description of Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in the green wavelength region and maintaining good efficiency even under high temperature conditions.

Example embodiments also provide an image sensor including the photoelectric device (e.g., organic photoelectric device).

Example embodiments also provide an electronic device including the image sensor.

According to example embodiments, a compound is represented by Chemical Formula 1.

[Chemical Formula 1]

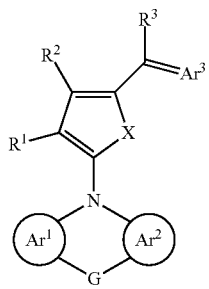

In Chemical Formula 1, $Ar^1$ and $Ar^2$ are each independently a substituted or unsubstituted C6 to C30 arene group, a substituted or unsubstituted C3 to C30 heteroarene group, or a condensed ring thereof, $Ar^3$ is a substituted or unsubstituted hydrocarbon cyclic group having two carbonyl groups, a substituted or unsubstituted heterocyclic group having two carbonyl groups, or a fused ring thereof, X is Se, Te, or $SiR^aR^b$ (wherein $R^a$ and $R^b$ are each independently hydrogen, a halogen, a substituted or unsubstituted C1 to C10 alkyl group, or a substituted or unsubstituted C6 to C10 aryl group), $R^1$ to $R^3$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein $R^1$ and $R^2$ are each independently present or linked with each other to provide a ring, G is $-SiR^eR^f-$, $-GeR^gR^h-$, $-CR^{cc}R^{dd}-$, $-SiR^{ee}R^{ff}-$, $-GeR^{gg}R^{hh}-$, $-(C(R^{ii})=C(R^{jj}))-$, or $G'(CR^xR^y)_n$, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and a melting point ($T_m$) and a deposition temperature ($T_s$) of the compound satisfy Equation 1.

$$T_m - T_s \geq 40° C. \quad \text{[Equation 1]}$$

In $G'(CR^xR^y)_n$, $G'$ may be $-C-$, $-Si-$, $-Ge-$, or $-C=C-$. $R^x$ and $R^y$ each independently may be hydrogen, a halogen, a substituted or unsubstituted C1 to C10 alkyl group, or a substituted C6 to C10 aryl group. And n may be an integer of 3 to 8.

In some embodiments, the ring provided by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure.

In some embodiments, the compound represented by Chemical Formula 1 may be a compound represented by Chemical Formula 1A.

[Chemical Formula 1A]

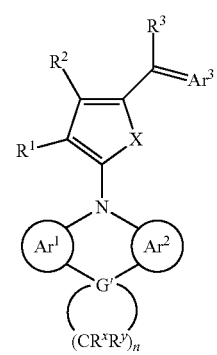

In Chemical Formula 1A,

Ar$^1$, Ar$^2$, Ar$^3$, X, and R$^1$ to R$^3$ are the same as in Chemical Formula 1, G$^i$ is —C—, —Si—, —Ge—, or —C≡C—, R$^x$ and R$^y$ are each independently hydrogen, a halogen, a substituted or unsubstituted C1 to C10 alkyl group, or a substituted or unsubstituted C6 to C10 aryl group, and n is an integer of 3 to 8.

In some embodiments, in Chemical Formula 1A, at least one non-adjacent C(R$^x$R$^y$) may be replaced by at least one of —N—, —NR$^a$— (wherein R$^a$ is hydrogen, a halogen, a substituted or unsubstituted C1 to C10 alkyl group, or a substituted or unsubstituted C6 to C10 aryl group), —O—, —S—, —Se—, and —Te—.

In some embodiments, in Chemical Formula 1, Ar$^3$ may be a cyclic group represented by one of Chemical Formula 2A to Chemical Formula 2D.

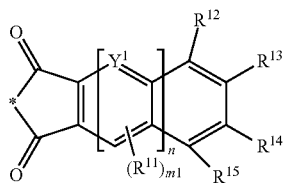

[Chemical Formula 2A]

In Chemical Formula 2A,

Y$^1$ is N or CR$^a$ (wherein R$^a$ is hydrogen, deuterium, or a substituted or unsubstituted C1 to C10 alkyl group), R$^{11}$, R$^{12}$, R$^{13}$, R$^{14}$, and R$^{15}$ are hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or a pair of R$^{12}$ and R$^{13}$ Or a pair of R$^{14}$ and R$^{15}$ is each independently linked with each other to provide a fused aromatic ring, m1 is 0 or 1, n is 0 or 1, and

* is a linking point.

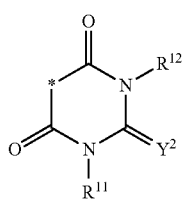

[Chemical Formula 2B]

In Chemical Formula 2B,

Y$^2$ is O, S, Se, Te, or C(R$^a$)(CN) (wherein R$^a$ is hydrogen, a cyano group (—CN), or a C1 to C10 alkyl group), R$^{11}$ and R$^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

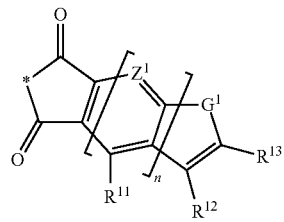

[Chemical Formula 2C]

In Chemical Formula 2C,

G$^1$ is —O—, —S—, —Se—, —Te—, —SiR$^x$R$^y$—, or —GeR$^z$R$^w$—, wherein R$^x$, R$^y$, R$^z$, and R$^w$ are the same or different and are each independently hydrogen, a halogen, a substituted or unsubstituted C1 to C10 alkyl group, or a substituted or unsubstituted C6 to C10 aryl group, Z$^1$ is N or CR$^a$ (wherein R$^a$ is hydrogen or a substituted or unsubstituted C1 to C10 alkyl group), R$^{11}$, R$^{12}$, and R$^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein R$^{12}$ and R$^{13}$ are each independently present or linked with each other to provide a fused aromatic ring, n is 0 or 1, and

* is a linking point.

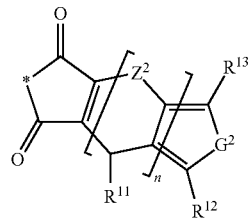

[Chemical Formula 2D]

In Chemical Formula 2D,

G$^2$ is —O—, —S—, —Se—, —Te—, —SiR$^x$R$^y$—, or —GeR$^z$R$^w$—, wherein R$^x$, R$^Y$, R$^z$, and R$^w$ are the same or different and are each independently hydrogen, a halogen, a substituted or unsubstituted C1 to C10 alkyl group, or a substituted or unsubstituted C6 to C10 aryl group, Z$^2$ is NR$^a$, CR$^b$R$^c$, O, S, Se, Te, S(=O), S(=O)$_2$, SiR$^d$R$^e$, or GeR$^f$R$^g$ (wherein R$^a$, R$^b$, R$^c$, R$^d$, R$^e$, R$^d$, R$^e$, R$^f$, and R$^g$ are hydrogen or a substituted or unsubstituted C1 to C10 alkyl group), R$^{11}$, R$^{12}$, and R$^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

In some embodiments, in Chemical Formula 1, at least one of Ar$^1$ and Ar$^2$ may include a heteroatom at position 1 and the heteroatom may be nitrogen (N), sulfur (S), or selenium (Se).

In some embodiments, an electron donor moiety (e.g.,

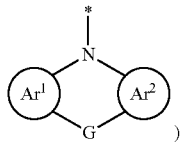

)

of the N-containing hetero aromatic ring of Chemical Formula 1 may be represented by one of Chemical Formula 4A to Chemical Formula 4E.

[Chemical Formula 4A]

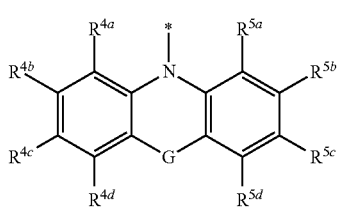

In Chemical Formula 4A,

G may be the same as in Chemical Formula 1, and $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

[Chemical Formula 4B]

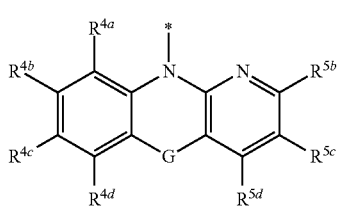

In Chemical Formula 4B,

G may be the same as in Chemical Formula 1, $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring, and optionally two adjacent groups of $R^{5b}$ to $R^{5d}$ are linked with each other to provide a 5-membered aromatic ring or a 6-membered aromatic ring.

[Chemical Formula 4C]

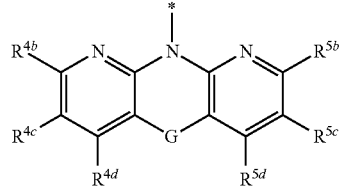

In Chemical Formula 4C,

G may be the same as in Chemical Formula 1, $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4b}$ to $R^{4d}$ are linked with each other to provide a 5-membered aromatic ring or a 6-membered aromatic ring, and optionally two adjacent groups of $R^{5b}$ to $R^{5d}$ are linked with each other to provide a 5-membered aromatic ring or a 6-membered aromatic ring.

[Chemical Formula 4D]

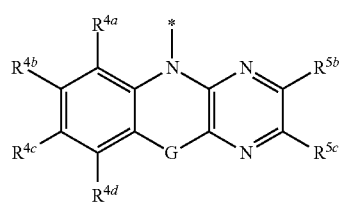

In Chemical Formula 4D,

G may be the same as in Chemical Formula 1, and $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring.

[Chemical Formula 4E]

In Chemical Formula 4E,

G may be the same as in Chemical Formula 1, $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring.

In some embodiments, an electron donor moiety of the N-containing hetero aromatic ring of Chemical Formula 1 may be represented by Chemical Formula 4F.

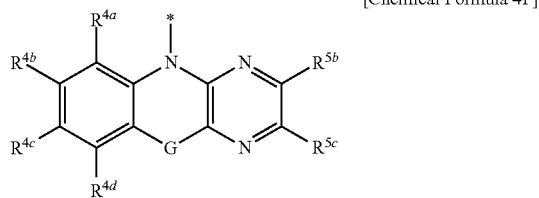

[Chemical Formula 4F]

In Chemical Formula 4F,

G may be the same as in Chemical Formula 1, $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring, and optionally two adjacent groups of $R^{5b}$ and $R^{5c}$ are linked with each other to provide a 5-membered aromatic ring or a 6-membered aromatic ring.

In some embodiments, an electron donor moiety of the N-containing hetero aromatic ring of Chemical Formula 1 may be represented by Chemical Formula 4G.

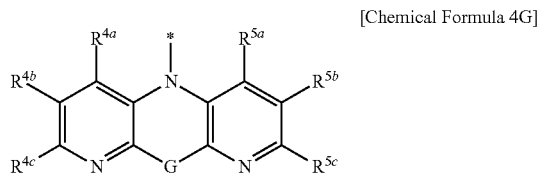

[Chemical Formula 4G]

In Chemical Formula 4G,

G may be the same as in Chemical Formula 1, $R^{4a}$ to $R^{4c}$ and $R^{5a}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4c}$ are linked with each other to provide a 5-membered aromatic ring or a 6-membered aromatic ring, and optionally two adjacent groups of $R^{5a}$ to $R^{5c}$ are linked with each other to provide a 5-membered aromatic ring or a 6-membered aromatic ring.

In some embodiments, an electron donor moiety of the N-containing hetero aromatic ring of Chemical Formula 1 may be represented by Chemical Formula 4H.

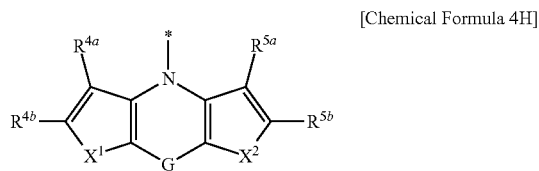

[Chemical Formula 4H]

In Chemical Formula 4H,

G may be the same as in Chemical Formula 1, $X^1$ and $X^2$ are each independently O, S, Se, Te, or $NR^a$ ((wherein $R^a$ is hydrogen, a halogen, a substituted or unsubstituted C1 to C10 alkyl group, or a substituted or unsubstituted C6 to C10 aryl group), $R^{4a}$, $R^{4b}$, $R^{5a}$, and $R^{5b}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ and $R^{4b}$ are linked with each other to provide a 5-membered aromatic ring or a 6-membered aromatic ring, and optionally two adjacent groups of $R^{5a}$ and $R^{5b}$ are linked with each other to provide a 5-membered aromatic ring or a 6-membered aromatic ringIn some embodiments, the compound may have a maximum absorption wavelength ($\lambda_{max}$) in a wavelength region of greater than or equal to about 520 nm and less than about 600 nm.

In some embodiments, the compound may exhibit a light absorption curve having a full width at half maximum (FWHM) of about 50 nm to about 120 nm, in a thin film state.

According to another embodiment, a photoelectric device (e.g., organic photoelectric device) includes a first electrode and a second electrode facing each other and an active layer between the first electrode and the second electrode. The active layer may include the compound represented by Chemical Formula 1.

According to another embodiment, an image sensor includes the photoelectric device.

In some embodiments, the image sensor may include a semiconductor substrate integrated with a plurality of first photo-sensing devices and a plurality of second photo-sensing devices. The plurality of first photo-sensing devices may be configured to sense light in a blue wavelength region and the plurality of second photo-sensing devices and may be configured to sense light in a red wavelength region. The photoelectric device may be on the semiconductor substrate and configured to selectively sense light in a green wavelength region.

In some embodiments, the first photo-sensing device and the second photo-sensing device may be stacked in a vertical direction in the semiconductor substrate.

In some embodiments, the image sensor may further include a color filter layer on the semiconductor substrate. The color filter layer may include a blue filter that is configured to selectively transmit light in a blue wavelength region and a red filter that is configured selectively transmit light in a red wavelength region.

In some embodiments, the image sensor may include a green photoelectric device, a blue photoelectric device, and a red photoelectric device that may be stacked. The green photoelectric device may be an organic photoelectric device and may be the photoelectric device. The blue photoelectric device may be configured to selectively absorb light in a blue wavelength region and the red photoelectric device may be configured to selectively absorb light in a red wavelength region.

According to another embodiment, an electronic device includes the image sensor.

According to some example embodiments, a compound represented by Chemical Formula 1 is provided.

[Chemical Formula 1]

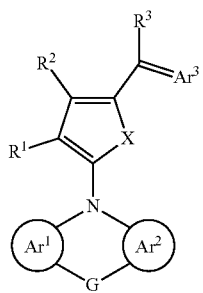

In Chemical Formula 1,

Ar$^1$ and Ar$^2$ are each independently a substituted or unsubstituted C6 to C30 arene group, a substituted or unsubstituted C3 to C30 heteroarene group, or a condensed ring thereof, Ar$^3$ is a substituted or unsubstituted hydrocarbon cyclic group having two carbonyl groups, a substituted or unsubstituted heterocyclic group having two carbonyl groups, or a fused ring thereof, X is Se, Te, or SiR$^a$R$^b$ (wherein R$^a$ and R$^b$ are each independently hydrogen, a halogen, a substituted or unsubstituted C1 to C10 alkyl group, or a substituted or unsubstituted C6 to C10 aryl group), R$^1$ to R$^3$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein R$^1$ and R$^2$ are each independently present or linked with each other to provide a ring, G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, —(C(R$^{ii}$)=C(R$^{jj}$))—, or G'(CR$^x$R$^y$)$_n$, wherein R$^e$, R$^f$, R$^g$, and R$^h$ are each independently hydrogen, a halogen, a substituted or unsubstituted C1 to C10 alkyl group, or a substituted or unsubstituted C6 to C10 aryl group, wherein the pairs of R$^{cc}$ and R$^{dd}$, R$^{ee}$ and R$^{ff}$, R$^{gg}$ and R$^{hh}$, and R$^{ii}$ and R$^{jj}$ are linked with each other to provide a ring, wherein, in G'(CR$^x$R$^y$)$_n$, G' is —C—, —Si—, —Ge—, or —C=C—, R$^x$ and R$^y$ are each independently hydrogen, a halogen, a substituted or unsubstituted C1 to C10 alkyl group, or a substituted or unsubstituted C6 to C10 aryl group, and n is an integer of 3 to 8.

An electron donor moiety of the N-containing hetero aromatic ring of Chemical Formula 1 may be represented by one of Chemical Formulas 4A to 4H:

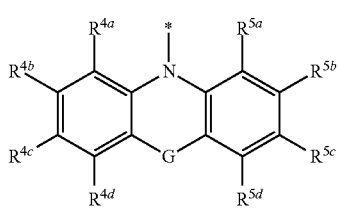

[Chemical Formula 4A]

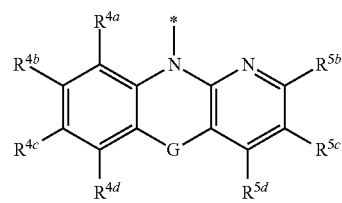

[Chemical Formula 4B]

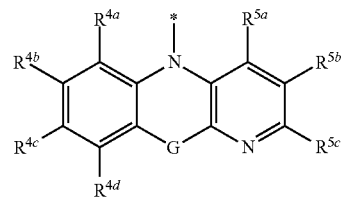

[Chemical Formula 4C]

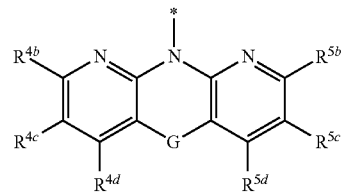

[Chemical Formula 4D]

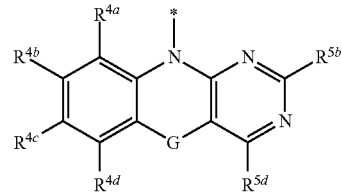

[Chemical Formula 4E]

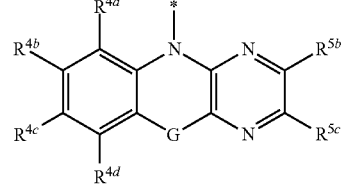

[Chemical Formula 4F]

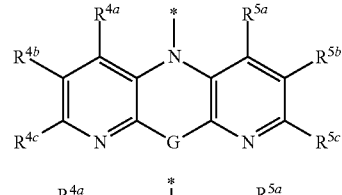

[Chemical Formula 4G]

[Chemical Formula 4H]

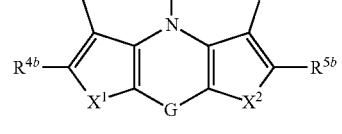

In Chemical Formulas 4A to 4H,

G is the same as in Chemical Formula 1,

R$^{4a}$ to R$^{4d}$ and R$^{5a}$ to R$^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of R$^{4a}$ to R$^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and wherein, in Chemical Formula 4H, $X^1$ and $X^2$ are each independently O, S, Se, Te or $NR^a$ (wherein $R^a$ is hydrogen, a halogen, a substituted or unsubstituted C1 to C10 alkyl group, or a substituted or unsubstituted C6 to C10 aryl group).

In some embodiments, in Chemical Formula 1, $Ar^3$ may be a cyclic group represented by one of Chemical Formulas 2A to 2D:

[Chemical Formula 2A]

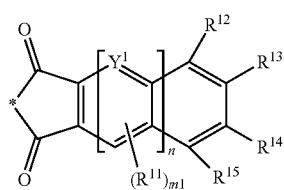

[Chemical Formula 2B]

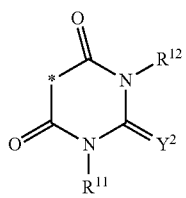

[Chemical Formula 2C]

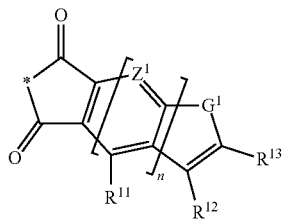

[Chemical Formula 2D]

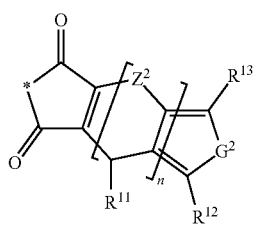

In Chemical Formulas 2A to 2D, * is a linking point and each substituent may be the same as discussed above for Chemical Formulas 2A to 2D.

In some embodiments, the compound may have a maximum absorption wavelength ($\lambda_{max}$) in a wavelength region of greater than or equal to about 520 nm and less than or equal to about 600 nm, and the compound may exhibit a light absorption curve having a full width at half maximum (FWHM) of about 50 nm to about 120 nm, in a thin film state.

In some embodiments, a photoelectric device may include a first electrode and a second electrode facing each other, and an active layer between the first electrode and the second electrode. The active layer may include the compound represented by Chemical Formula 1.

An image sensor may include the photoelectric device.

Compounds according to example embodiments may selectively absorb light in a green wavelength region and may have thermal stability. Compounds according to example embodiments may improve efficiency by increasing wavelength selectivity of the green wavelength region and providing photoelectric devices, image sensors and electronic devices that do not deteriorate performance even at high temperature processes due to improved thermal stability.

DETAILED DESCRIPTION

Figure 1:
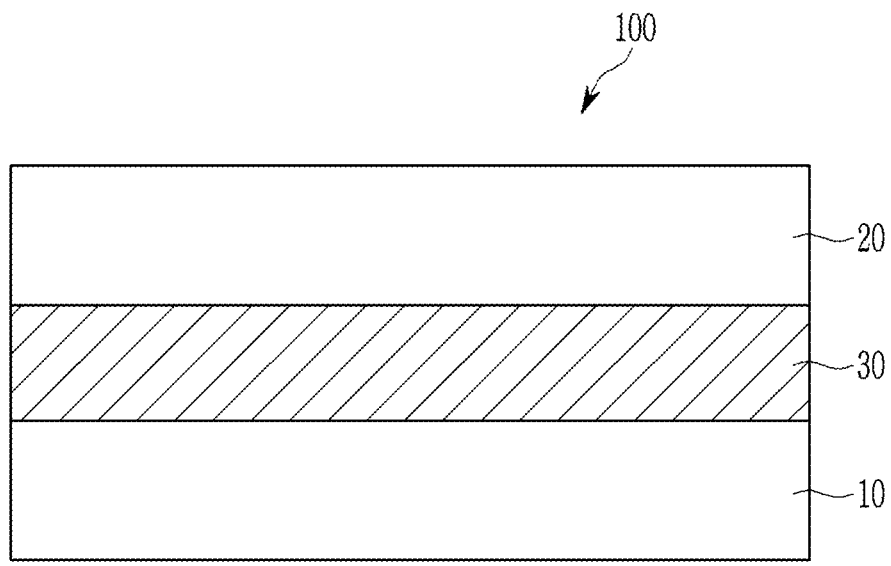
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements also may be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; A and B; A and C; B and C; or A, B and C).

As used herein, when specific definition is not otherwise provided, "substituted" refers to replacement of a hydrogen of a compound or a functional group by a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, =S, or a combination thereof.

As used herein, when specific definition is not otherwise provided, "hetero" refers to one including 1 to 3 heteroatoms selected from N, O, S, Se, Te, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a substituent including all element of the functional group having p-orbitals which form conjugation, and may be a monocyclic, polycyclic or fused ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as =CR$^{x'}$—(CR$^x$R$^y$)$_p$—CR$^{y'}$(CN)$_2$ wherein R$^x$, R$^y$, R$^{x'}$, and R$^{y'}$ are each independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, "hydrocarbon cyclic group" refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a cyclic group including a heteroatom selected from N, O, S, Se, Te, P, and Si instead of 1 to 3 carbon atoms in a cyclic group selected from an arene group (e.g., C6 to C30 aryl group, C6 to C20 aryl group or C6 to C10 aryl group), an alicyclic hydrocarbon group (e.g., C3 to C30 cycloalkyl group, C3 to C20 cycloalkyl group or C3 to C10 cycloalkyl group), or a fused ring thereof. At least one carbon atom of the heterocyclic group also may be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P and Si in a cyclic group.

As used herein, "C6 to C30 aromatic hydrocarbon group" includes a C6 to C30 aryl group such as a phenyl group, a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited to.

As used herein, "5-membered aromatic ring" refers to a 5-membered ring group (e.g., C5 aryl group) having a conjugation structure or a 5-membered heterocyclic group (e.g., C2 to C4 heteroaryl group) having a conjugation structure. As used herein, "6-membered aromatic ring" refers to a 6-membered ring group (e.g., C6 aryl group) having a conjugation structure or a 6-membered heterocyclic group (e.g., C2 to C5 heteroaryl groups) having a conjugation structure, but is not limited thereto. The aromatic ring may include the 5-membered aromatic ring or the 6-membered aromatic ring, but is not limited thereto.

Hereinafter, a compound according to an embodiment is described. The compound is represented by Chemical Formula 1.

[Chemical Formula 1]

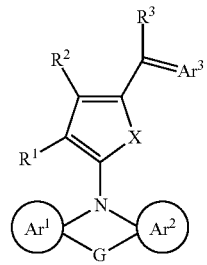

In Chemical Formula 1,

Ar$^1$ and Ar$^2$ are each independently a substituted or unsubstituted C6 to C30 arene group, a substituted or unsubstituted C3 to C30 heteroarene group, or a condensed ring thereof, Ar$^3$ is a substituted or unsubstituted hydrocarbon cyclic group having two carbonyl groups, a substituted or unsubstituted heterocyclic group having two carbonyl groups, or a fused ring thereof, X is Se, Te, or SiR$^a$R$^b$ (wherein R$^a$ and R$^b$ is each independently hydrogen, a halogen, a substituted or unsubstituted C1 to C10 alkyl group, or a substituted or unsubstituted C6 to C10 aryl group), R$^1$ to R$^3$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein R$^1$ and R$^2$ are each independently present or linked with each other to provide a ring, G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, —(C(R$^{ii}$)=C(R$^{jj}$))—, or G'(CR$^x$R$^y$)$_n$, wherein R$^e$, R$^f$, R$^g$, and R$^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and a melting point ($T_m$) and a deposition temperature ($T_s$) of the compound satisfy Equation 1.

In $G'(CR^xR^y)_n$, $G'$ may be —C—, —Si—, —Ge—, or —C=C—. $R^x$ and $R^Y$ each independently may be hydrogen, a halogen, a substituted or unsubstituted C1 to C10 alkyl group, or a substituted C6 to C10 aryl group. And n may be an integer of 3 to 8.

$$T_m - T_s \geq 40° \text{ C.} \quad \text{[Equation 1]}$$

The compound represented by Chemical Formula 1 includes an N-containing hetero aromatic ring as an electron donor moiety, an X-containing 5-membered ring as a linker, and an electron acceptor moiety represented by $Ar^3$.

In Chemical Formula 1, the cyclic group represented by $Ar^3$ includes at least two carbonyl groups as an electron acceptor moiety. $Ar^3$ may be a substituted or unsubstituted hydrocarbon cyclic group having two carbonyl groups, a substituted or unsubstituted heterocyclic group having two carbonyl groups, or a fused ring thereof. In an embodiment, $Ar^3$ may be a substituted or unsubstituted 5-membered aromatic ring, a substituted or unsubstituted 6-membered aromatic ring, or a condensed ring of two or more.

In Chemical Formula 1, the ring formed by linking $R^{cc}$ and $R^{dd}$, $R^{ee}$ and $R^{ff}$, $R^{gg}$ and $R^{hh}$, or $R^{ii}$ and $R^{jj}$ with each other may have a spiro structure or a fused ring structure and may be a cyclic structure composed of three to eight atoms. For example, it may be a 5-membered or 6-membered ring. Optionally, the ring may also include at least one heteroatom selected from N, O, S, Se, and Te.

In an embodiment, the ring may be a C3 to C8 cycloalkyl group, a C3 to C8 heterocycloalkyl group, a C3 to C8 aryl group, or a C3 to C8 heteroaryl group.

The compound represented by Chemical Formula 1 may be a compound represented by Chemical Formula 1A.

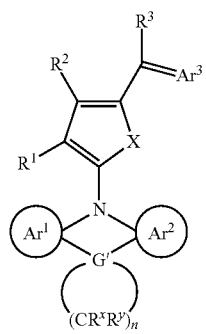

[Chemical Formula 1A]

$Ar^1$, $Ar^2$, $Ar^3$, X, and $R^1$ to $R^3$ are the same as in Chemical Formula 1, $G'$ is —C—, —Si—, —Ge—, or —C=C—, $R^x$ and $R^y$ are each independently hydrogen, a halogen, a substituted or unsubstituted C1 to C10 alkyl group, or a substituted or unsubstituted C6 to C10 aryl group, and n is an integer of 3 to 8, for example 5 or 6.

In Chemical Formula 1A, at least one non-adjacent $C(R^xR^y)$ may be replaced by at least one of —N—, —$NR^a$— (wherein $R^a$ is hydrogen, a halogen, a substituted or unsubstituted C1 to C10 alkyl group, or a substituted or unsubstituted C6 to C10 aryl group), —O—, —S—, —Se—, and —Te—. In this case, a ring including a heteroatom may be formed.

In Chemical Formula 1, $Ar^3$ may be a cyclic group represented by one of Chemical Formula 2A to Chemical Formula 2D.

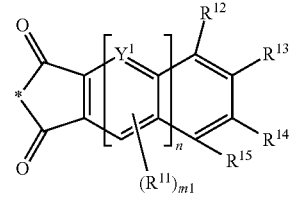

[Chemical Formula 2A]

In Chemical Formula 2A, $Y^1$ is N or $CR^a$ (wherein $R^a$ is hydrogen, deuterium, or a substituted or unsubstituted C1 to C10 alkyl group), $R^{11}$, $R^{12}$, $R^{13}$, $R^{14}$, and $R^{15}$ are hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or a pair of $R^{12}$ and $R^{13}$ or a pair of $R^{14}$ and $R^{15}$ is each independently linked with each other to provide a fused aromatic ring, m1 is 0 or 1, n is 0 or 1, and

* is a linking point.

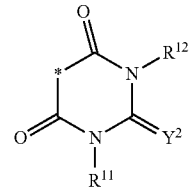

[Chemical Formula 2B]

In Chemical Formula 2B, $Y^2$ is each independently O, S, Se, Te, or $C(R^a)(CN)$ (wherein $R^a$ is hydrogen, a cyano group (—CN), or a C1 to C10 alkyl group), $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

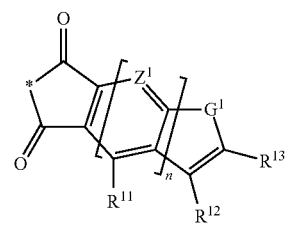

[Chemical Formula 2C]

In Chemical Formula 2C,

G$^1$ is —O—, —S—, —Se—, —Te—, —SiR$^x$R$^y$—, or —GeR$^z$R$^w$—, wherein R$^x$, R$^y$, R$^z$, and R$^w$ are the same or different and are each independently hydrogen, a halogen, a substituted or unsubstituted C1 to C10 alkyl group, or a substituted or unsubstituted C6 to C10 aryl group, Z$^1$ is N or CR$^a$ (wherein R$^a$ is hydrogen or a substituted or unsubstituted C1 to C10 alkyl group), R$^{11}$, R$^{12}$, and R$^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein R$^{12}$ and R$^{13}$ are each independently present or linked with each other to provide a fused aromatic ring, n is 0 or 1, and

* is a linking point.

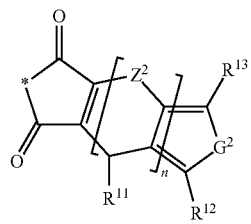

[Chemical Formula 2D]

In Chemical Formula 2D,

G$^2$ is —O—, —S—, —Se—, —Te—, —SiR$^x$R$^y$—, or —GeR$^z$R$^w$—, wherein R$^x$, R$^Y$, R$^z$, and R$^w$ are the same or different and are each independently hydrogen, a halogen, a substituted or unsubstituted C1 to C10 alkyl group, or a substituted or unsubstituted C6 to C10 aryl group, Z$^2$ is NR$^a$, CR$^b$R$^c$, O, S, Se, Te, S(=O), S(=O)$_2$, SiR$^d$R$^e$, or GeR$^f$R$^g$ (wherein R$^a$, R$^b$, R$^c$, R$^d$, R$^e$, R$^d$, R$^e$, R$^f$, and R$^g$ are hydrogen or a substituted or unsubstituted C1 to C10 alkyl group), R$^{11}$, R$^{12}$, and R$^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

The cyclic group represented by Chemical Formula 2A may be for example a cyclic group represented by Chemical Formula 2A-1 or 2A-2.

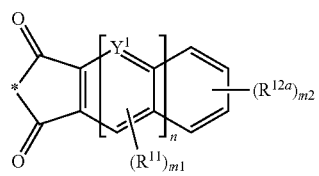

[Chemical Formula 2A-1]

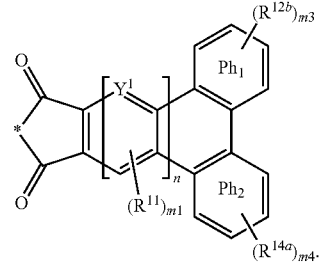

[Chemical Formula 2A-2]

In Chemical Formulas 2A-1 and 2A-2,

Y$^1$, R$^{11}$, m1, and n are the same as in Chemical Formula 2A,

R$^{12a}$, R$^{12b}$, and R$^{14a}$ are each independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m2, m3, and m4 are each independently an integer of 0 to 4, and Ph1 and Ph2 refer to fused phenylene rings and one of Ph1 and Ph2 may be optionally omitted.

The cyclic group represented by Chemical Formula 2B may be, for example, a cyclic group represented by Chemical Formula 2B-1, 2B-2, or 2B-3.

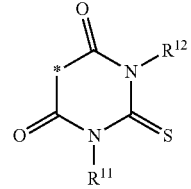

[Chemical Formula 2B-1]

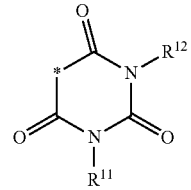

[Chemical Formula 2B-2]

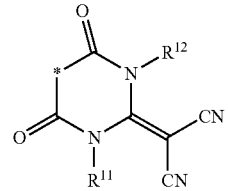

[Chemical Formula 2B-3]

In Chemical Formulas 2B-1, 2B-2, and 2B-3,

R$^{11}$ and R$^{12}$ are the same as in Chemical Formula 2B.

Ar$^1$ and Ar$^2$ of the N-containing hetero aromatic ring are linked by G to provide a single conjugation structure as a whole to improve thermal stability of the compound. This conjugation structure may be formed by fusing three or four 5- or 6-membered aromatic rings, but is not limited thereto.

Ar$^1$ and Ar$^2$ may be a substituted or unsubstituted C6 to C30 arene group, a substituted or unsubstituted C3 to C30 heteroarene group, or a condensed ring thereof in which aromatic rings are fused with each other, for example a substituted or unsubstituted C6 to C20 arene group, a substituted or unsubstituted C3 to C20 heteroarene group, or a condensed ring thereof.

In an embodiment, the arene group may be benzene, naphthalene, and anthracene. The heteroarene group may be pyrrole, pyrazole, imidazole, oxazole, isoxazole, thiazole, isothiazole, pyridine, pyridazine, pyrimidine, pyrazine, indole, quinoline, isoquinoline, naphthyridine, cinnoline, quinazoline, phthalazine, benzotriazine, pyridopyrazine, pyridopyrimidine, pyridopyridazine, thiophene, benzothiophene, selenophene, or benzoselenophene.

In Chemical Formula 1, X of the linker including the X-containing 5-membered ring and oxygen (O) of the carbonyl group in the electron acceptor moiety may increase an intramolecular interaction to improve absorption intensity at predetermined wavelengths.

In the linker including the X-containing 5-membered ring, $R^1$ and $R^2$ may each independently present and may be linked with each other to provide a ring. When forming a ring, the linker may be represented by Chemical Formula 3A or Chemical Formula 3B.

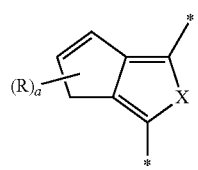

[Chemical Formula 3A]

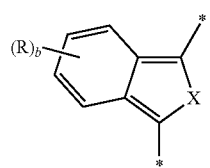

[Chemical Formula 3B]

In Chemical Formula 3A and Chemical Formula 3B,

X is Se, Te, or $SiR^aR^b$ (wherein $R^a$ and $R^b$ is each independently hydrogen, a halogen, a substituted or unsubstituted C1 to C10 alkyl group, or a substituted or unsubstituted C6 to C10 aryl group), R is hydrogen, a C1 to C10 alkyl group, a C6 to C10 aryl group, a C2 to C10 heteroaryl group, or a halogen, and a and b are each independently an integer of 1 to 4.

In Chemical Formula 1, at least one of $Ar^1$ and $Ar^2$ may include a heteroatom of nitrogen (N), sulfur (S), or selenium (Se) at the position 1. In this case, X, oxygen (O) of the carbonyl group in electron acceptor moiety, and the heteroatom at the position 1 of at least one $Ar^1$ and $Ar^2$ may increase a molecular interaction and thus may improve an absorption intensity at a predetermined wavelength.

The electron donor moiety of the N-containing hetero aromatic ring of Chemical Formula 1 may be represented by Chemical Formula 4A.

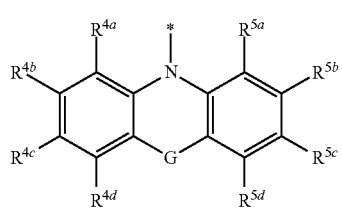

[Chemical Formula 4A]

In Chemical Formula 4A,

G is $-SiR^eR^f-$, $-GeR^gR^h-$, $-CR^{cc}R^{dd}-$, $-SiR^{ee}R^{ff}-$, $-GeR^{gg}R^{hh}-$, or $-(C(R^{ii})=C(R^{jj}))-$, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring. G also may be a $G'(CR^xR^y)_n$ group that is the same as in Chemical Formulas 1 and 1A described above.

The ring may include at least one heteroatom selected from N, O, S, Se, and Te.

Chemical Formula 4A may be represented by Chemical Formula 4A-1 or Chemical Formula 4A-2.

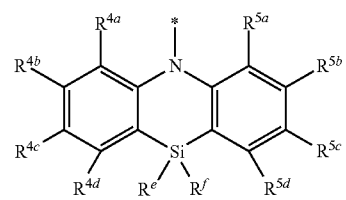

[Chemical Formula 4A-1]

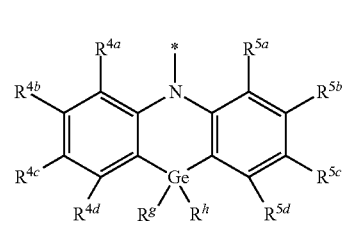

[Chemical Formula 4A-2]

In Chemical Formula 4A-1 and Chemical Formula 4A-2, $R^{4a}$ to $R^{4d}$ and $R^{5a}$ to $R^{5d}$ are the same as in Chemical Formula 4A, and $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4A, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4B.

[Chemical Formula 4B]

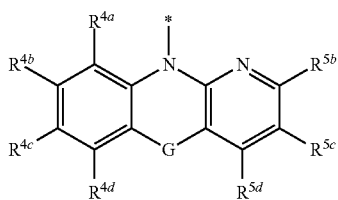

In Chemical Formula 4B,

G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein R$^e$, R$^f$, R$^g$, and R$^h$ are each independently hydrogen, a halogen, a substituted or unsubstituted C1 to C10 alkyl group, or a substituted or unsubstituted C6 to C10 aryl group, wherein the pairs of R$^{cc}$ and R$^{dd}$, R$^{ee}$ and R$^{ff}$, R$^{gg}$ and R$^{hh}$, and R$^{ii}$ and R$^{jj}$ are linked with each other to provide a ring, and R$^{4a}$ to R$^{4d}$ and R$^{5b}$ to R$^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of R$^{4a}$ to R$^{4d}$ are linked with each other to provide a 5-membered aromatic ring or a 6-membered aromatic ring and optionally two adjacent groups of R$^{5b}$ to R$^{5d}$ are linked with each other to provide a 5-membered aromatic ring or a 6-membered aromatic ring. G also may be a G'(CR$^x$R$^y$)$_n$ group that is the same as in Chemical Formulas 1 and 1A described above.

Chemical Formula 4B may be represented by Chemical Formula 4B-1 or Chemical Formula 4B-2.

[Chemical Formula 4B-1]

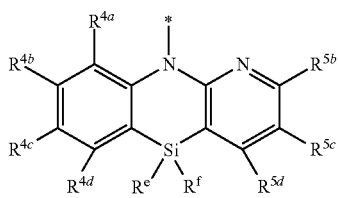

[Chemical Formula 4B-2]

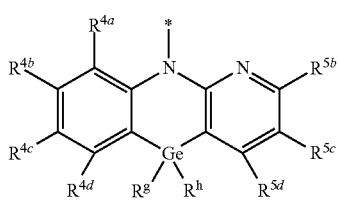

In Chemical Formula 4B-1 and Chemical Formula 4B-2, R$^{4a}$ to R$^{4d}$ and R$^{5b}$ to R$^{5d}$ are the same as in Chemical Formula 4B, and R$^e$, R$^f$, R$^g$, and R$^h$ are each independently hydrogen, a halogen, a substituted or unsubstituted C1 to C10 alkyl group, or a substituted or unsubstituted C6 to C10 aryl group.

In Chemical Formula 4B, the ring formed by linking R$^{cc}$ and R$^{dd}$, R$^{ee}$ and R$^{ff}$, R$^{gg}$ and R$^{hh}$, or R$^{ii}$ and R$^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4C.

[Chemical Formula 4C]

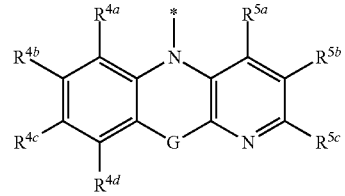

In Chemical Formula 4C,

G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein R$^e$, R$^f$, R$^g$, and R$^h$ are each independently hydrogen, a halogen, a substituted or unsubstituted C1 to C10 alkyl group, or a substituted or unsubstituted C6 to C10 aryl group, wherein the pairs of R$^{cc}$ and R$^{dd}$, R$^{ee}$ and R$^{ff}$, R$^{gg}$ and R$^{hh}$, and R$^{ii}$ and R$^{jj}$ are linked with each other to provide a ring, and R$^{4a}$ to R$^{4d}$ and R$^{5a}$ to R$^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of R$^{4a}$ to R$^{4d}$ are linked with each other to provide a 5-membered aromatic ring or a 6-membered aromatic ring and optionally two adjacent groups of R$^{5a}$ to R$^{5c}$ are linked with each other to provide a 5-membered aromatic ring or a 6-membered aromatic ring. G also may be a G'(CR$^x$R$^y$)$_n$ group that is the same as in Chemical Formulas 1 and 1A described above.

Chemical Formula 4C may be represented by Chemical Formula 4C-1 or Chemical Formula 4C-2.

[Chemical Formula 4C-1]

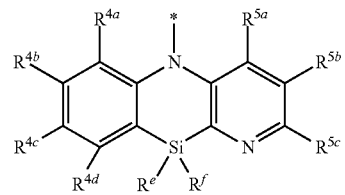

[Chemical Formula 4C-2]

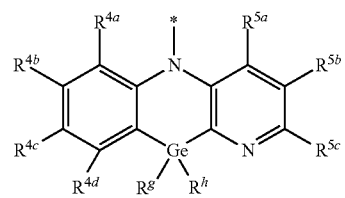

In Chemical Formula 4C-1 and Chemical Formula 4C-2, R$^{4b}$ to R$^{4d}$ and R$^{5a}$ to R$^{5c}$ are the same as in Chemical Formula 4C, $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4C, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4D.

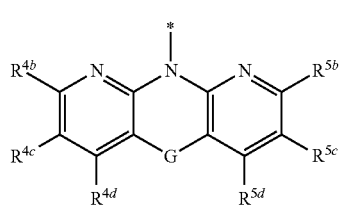

[Chemical Formula 4D]

In Chemical Formula 4D,

G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4b}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring. G also may be a G'(CR$^x$R$^y$)$_n$ group that is the same as in Chemical Formulas 1 and 1A described above.

Chemical Formula 4D may be represented by Chemical Formula 4D-1 or Chemical Formula 4D-2.

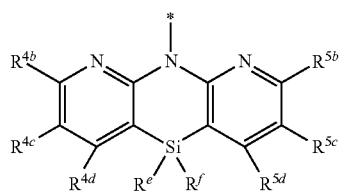

[Chemical Formula 4D-1]

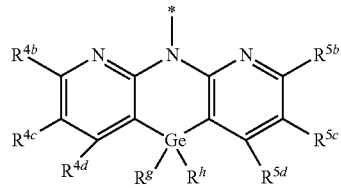

[Chemical Formula 4D-2]

In Chemical Formula 4D-1 and Chemical Formula 4D-2, $R^{4b}$ to $R^{4d}$ and $R^{5b}$ to $R^{5d}$ are the same as in Chemical Formula 4D, and $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4D, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4E.

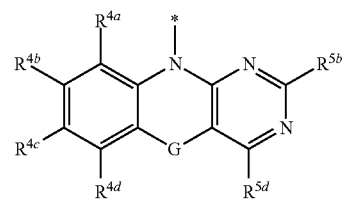

[Chemical Formula 4E]

In Chemical Formula 4E,

G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring. G also may be a G'(CR$^x$R$^y$)$_n$ group that is the same as in Chemical Formulas 1 and 1A described above.

Chemical Formula 4E may be represented by Chemical Formula 4E-1 or Chemical Formula 4E-2.

[Chemical Formula 4E-1]

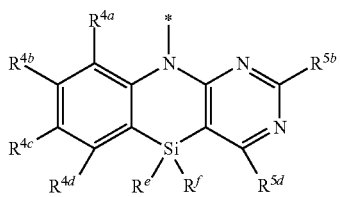

[Chemical Formula 4E-2]

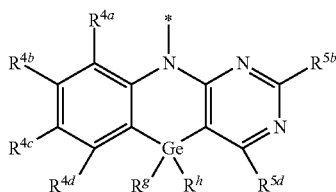

In Chemical Formula 4E-1 and Chemical Formula 4E-2, $R^{4a}$ to $R^{4d}$ and $R^{5b}$ and $R^{5d}$ are the same as in Chemical Formula 4E, and $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4E, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4F.

[Chemical Formula 4F]

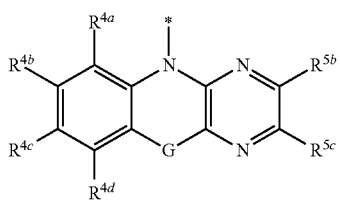

In Chemical Formula 4F,
G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4d}$ are linked with each other to provide a 5-membered aromatic ring or a 6-membered aromatic ring and optionally two adjacent groups of $R^{5b}$ and $R^{5c}$ are linked with each other to provide a 5-membered aromatic ring or a 6-membered aromatic ring. G also may be a G'(CR$^x$R$^y$)$_n$ group that is the same as in Chemical Formulas 1 and 1A described above.

Chemical Formula 4F may be represented by Chemical Formula 4F-1 or Chemical Formula 4F-2.

[Chemical Formula 4F-1]

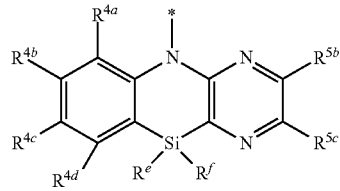

[Chemical Formula 4F-2]

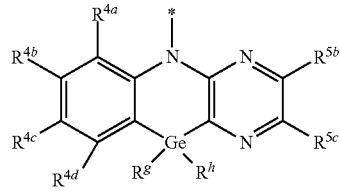

In Chemical Formula 4F-1 and Chemical Formula 4F-2, $R^{4a}$ to $R^{4d}$ and $R^{5b}$ and $R^{5c}$ are the same as in Chemical Formula 4F, $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4F, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4G.

[Chemical Formula 4G]

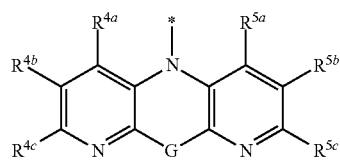

In Chemical Formula 4G,
G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, or —(C(R$^{ii}$)=C(R$^{jj}$))—, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, and $R^{4a}$ to $R^{4c}$ and $R^{5a}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ to $R^{4c}$ are linked with each other to provide a 5-membered aromatic ring or a 6-membered aromatic ring and optionally two adjacent groups of $R^{5a}$ to $R^{5c}$ are linked with each other to provide a 5-membered aromatic ring or a 6-membered aromatic ring. G also may be a $G'(CR^xR^y)_n$ group that is the same as in Chemical Formulas 1 and 1A described above.

Chemical Formula 4G may be represented by Chemical Formula 4G-1 or Chemical Formula 4G-2.

[Chemical Formula 4G-1]

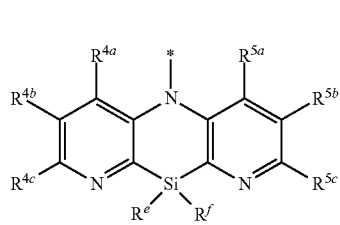

[Chemical Formula 4G-2]

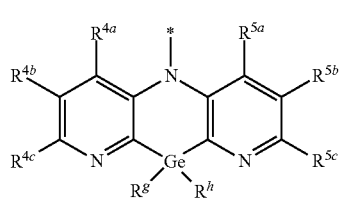

In Chemical Formula 4G-1 and Chemical Formula 4G-2, $R^{4a}$ to $R^{4c}$ and $R^{5a}$ to $R^{5c}$ are the same as in Chemical Formula 4G, $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4G, the ring formed by linking $R^{cc}$ and $R^{dd}$, $R^{ee}$ and $R^{ff}$, $R^{gg}$ and $R^{hh}$, Or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

The electron donor moiety of the N-containing hetero aromatic ring of Chemical Formula 1 may be represented by Chemical Formula 4H.

[Chemical Formula 4H]

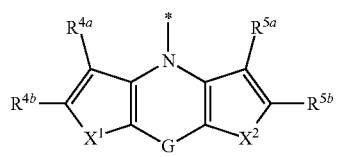

In Chemical Formula 4H,

G is $-SiR^eR^f-$, $-GeR^gR^h-$, $-CR^{cc}R^{dd}-$, $-SiR^{ee}R^{ff}-$, $-GeR^{gg}R^{hh}-$, or $-(C(R^{ii})=C(R^{jj}))-$, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, $R^{4a}$, $R^{4b}$, $R^{5a}$, and $R^{5b}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent groups of $R^{4a}$ and $R^{4b}$ are linked with each other to provide a 5-membered aromatic ring or a 6-membered aromatic ring and optionally two adjacent groups of $R^{5a}$ and $R^{5b}$ are linked with each other to provide a 5-membered aromatic ring or a 6-membered aromatic ring, $X^1$ and $X^2$ are each independently O, S, Se, Te, or $NR^a$ (wherein $R^a$ is hydrogen, a halogen, a substituted or unsubstituted C1 to C10 alkyl group, or a substituted or unsubstituted C6 to C10 aryl group). G also may be a $G'(CR^xR^y)_n$ group that is the same as in Chemical Formulas 1 and 1A described above.

In Chemical Formula 4H, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

Chemical Formula 4H may be represented by Chemical Formula 4H-1 or Chemical Formula 4H-2.

[Chemical Formula 4H-1]

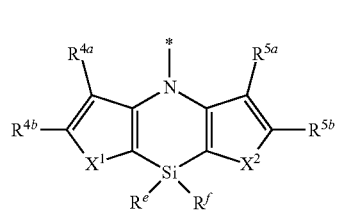

[Chemical Formula 4H-2]

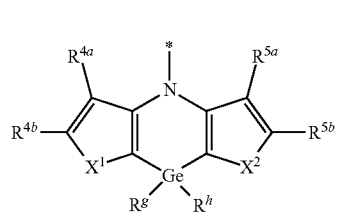

In Chemical Formula 4H-1 and Chemical Formula 4H-2, $R^{4a}$, $R^{4b}$, $R^{5a}$, $R^{5b}$, $X^1$, and $X^2$ are the same as in Chemical Formula 4H, and $R^e$, $R^f$, $R^g$, and $R^h$ are each independently hydrogen, a halogen, a substituted or unsubstituted C1 to C10 alkyl group, or a substituted or unsubstituted C6 to C10 aryl group.

In Chemical Formula 4H, the ring formed by linking $R^{cc}$ and $R^{dd}$, $R^{ee}$ and $R^{ff}$, $R^{gg}$ and $R^{hh}$, or $R^{ii}$ and $R^{jj}$ may have a spiro structure or a fused ring structure, and may be a 5-membered or 6-membered ring structure. Optionally, the ring may also include at least one heteroatom selected from N, O, S, Se, and Te.

Specific examples of the compound represented by Chemical Formula 1 may be compounds of Chemical Formula 5A, Chemical Formula 5B, Chemical Formula 5C, Chemical Formula 5D, and Chemical Formula 5E, but are not limited thereto.

[Chemical Formula 5A]
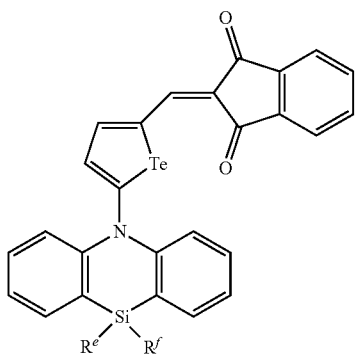
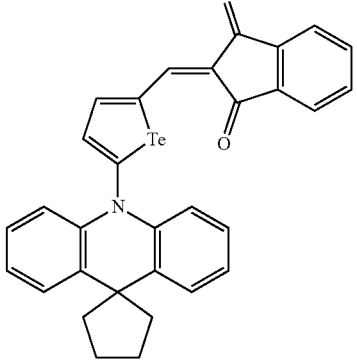
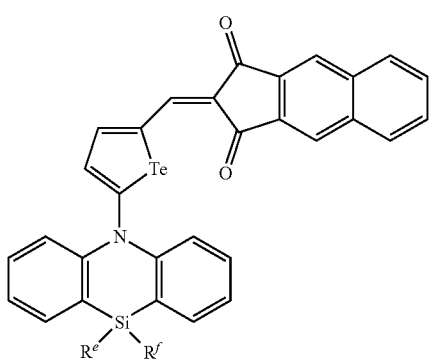
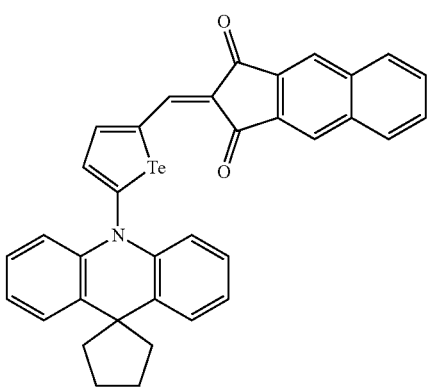
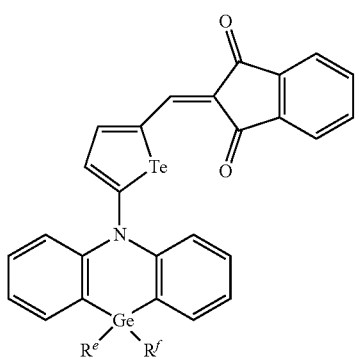
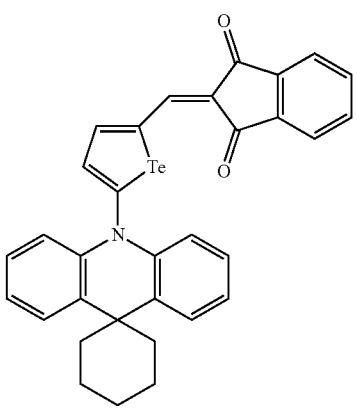
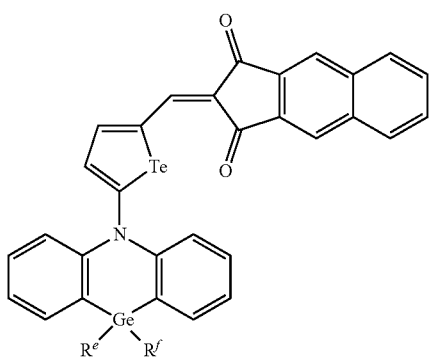
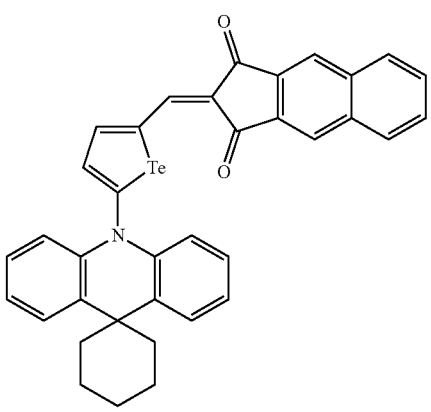

31
-continued
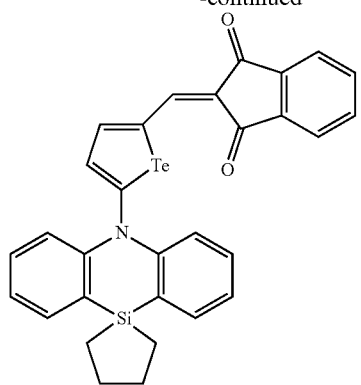
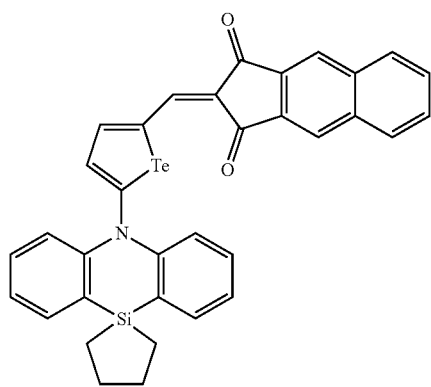
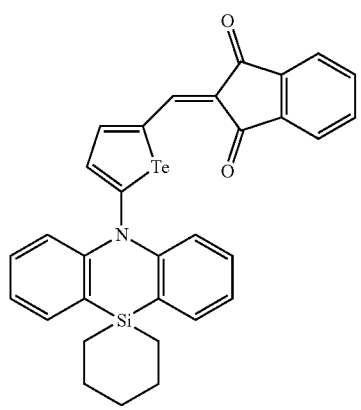
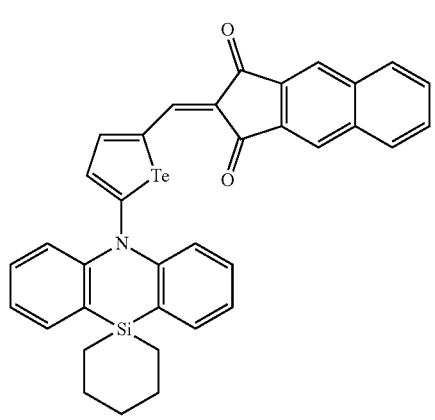
32
-continued
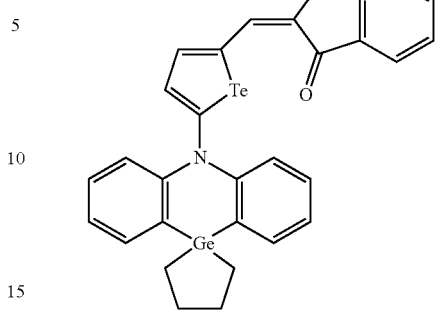
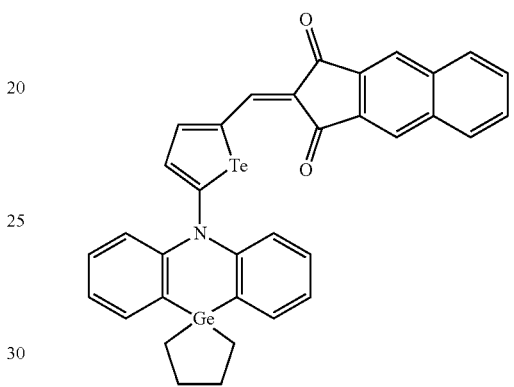
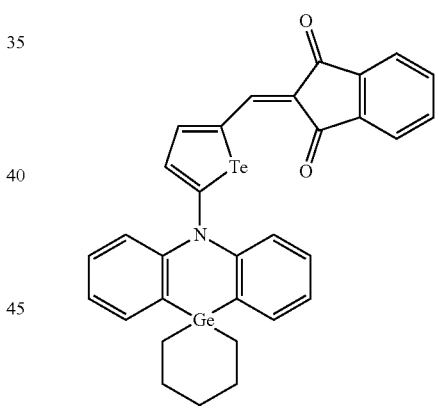
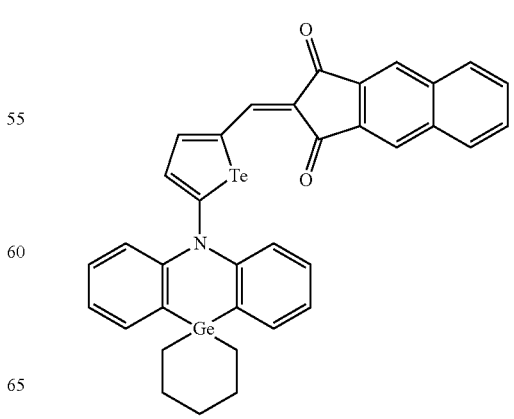

-continued

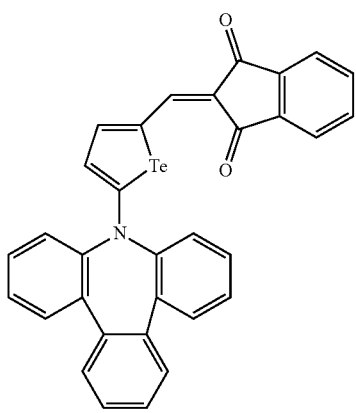

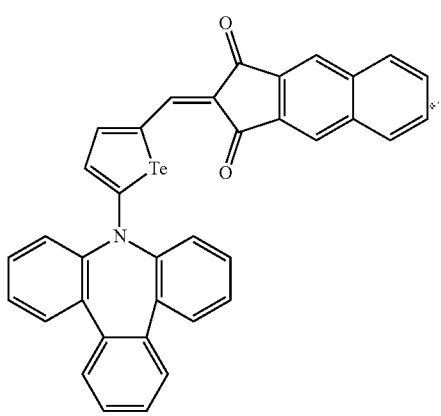

In Chemical Formula 5A, $R^e$, $R^f$, $R^g$, and $R^h$ are each independently hydrogen, a halogen, a substituted or unsubstituted C1 to C10 alkyl group, or a substituted or unsubstituted C6 to C10 aryl group, and hydrogen of each ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5B]

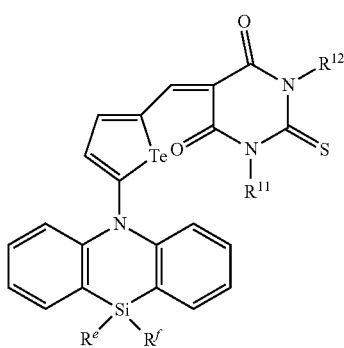

-continued

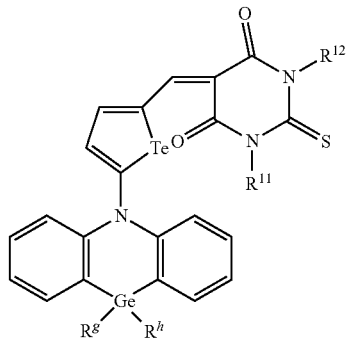

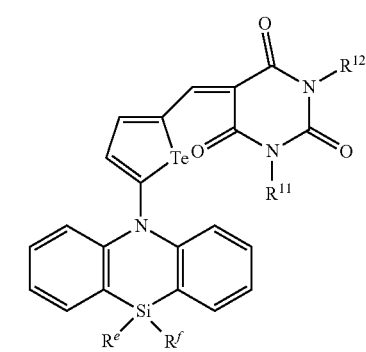

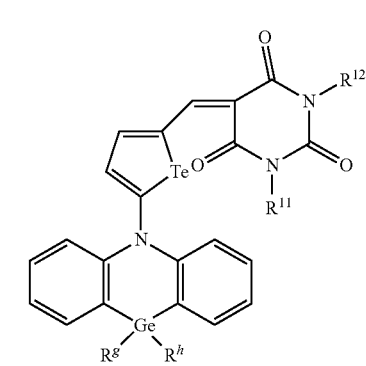

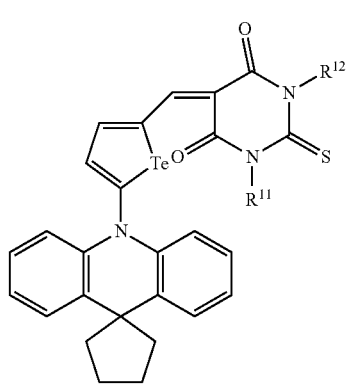

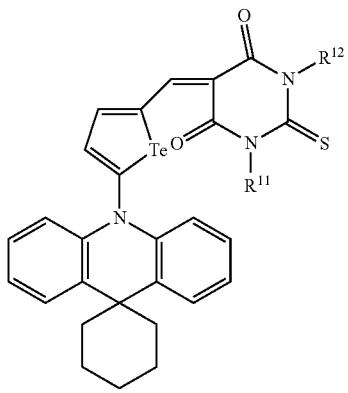
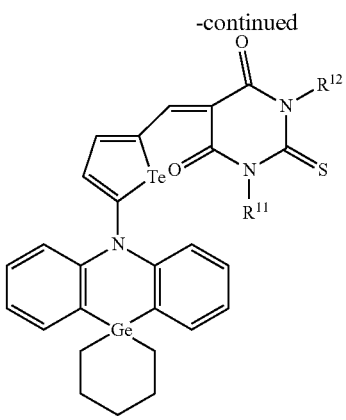
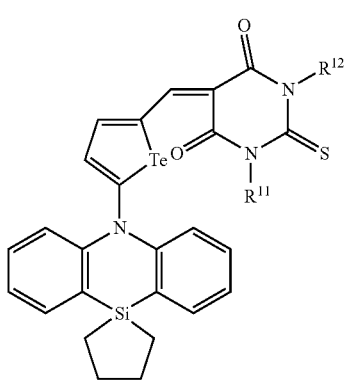
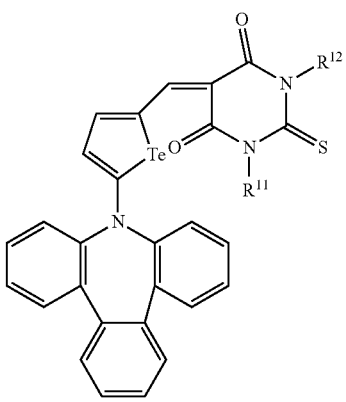
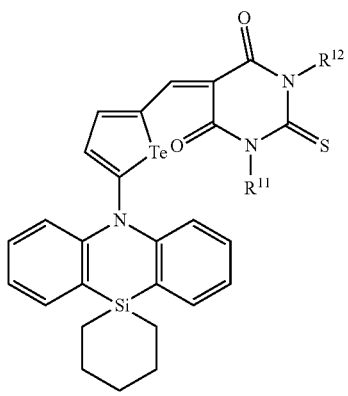
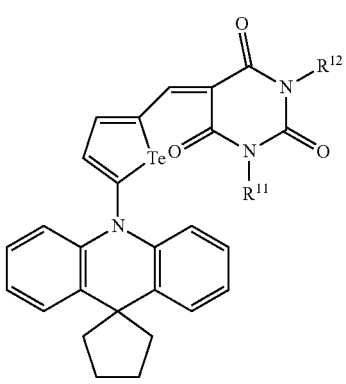
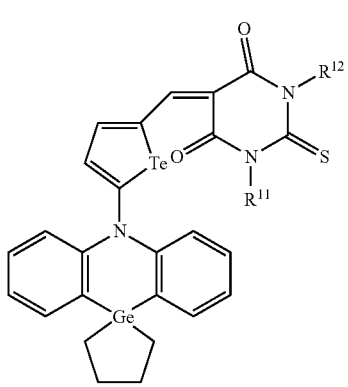
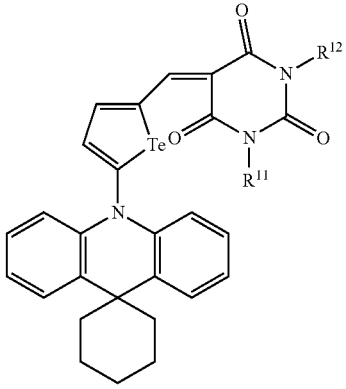

-continued

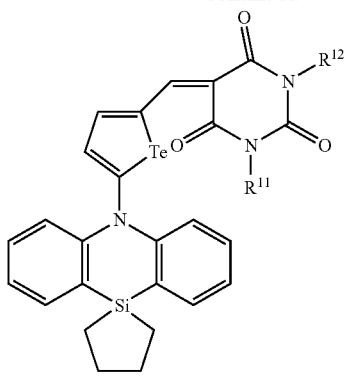

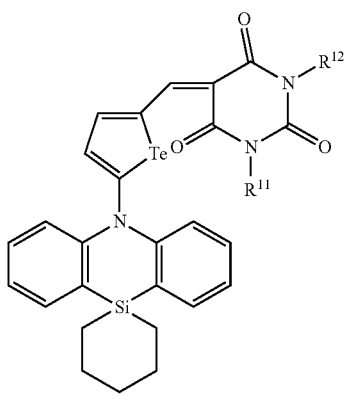

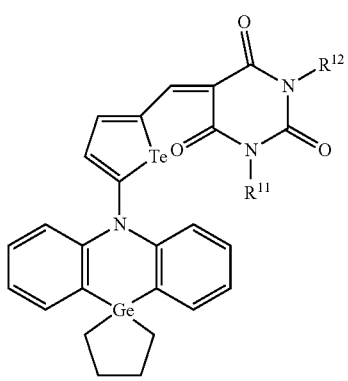

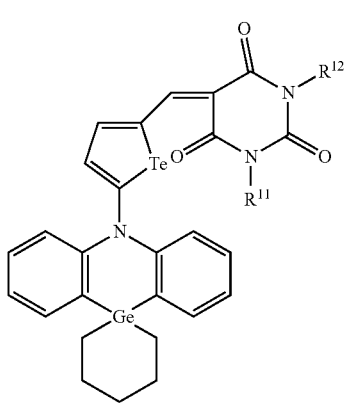

-continued

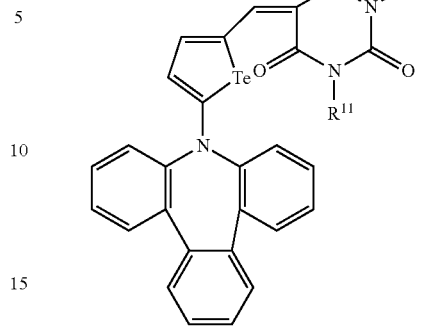

In Chemical Formula 5B, $R^{11}$ and $R^{12}$ are the same as in Chemical Formula 2B, le;3q$R^e$, $R^f$, $R^g$, and $R^h$ are each independently hydrogen, a halogen, a substituted or unsubstituted C1 to C10 alkyl group, or a substituted or unsubstituted C6 to C10 aryl group, and hydrogen of each ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 5C]

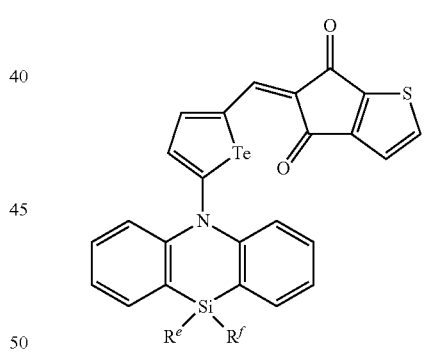

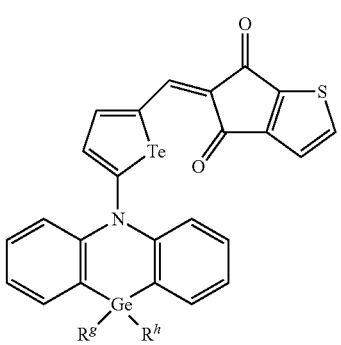

39

-continued

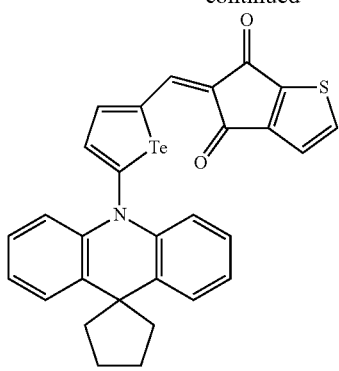

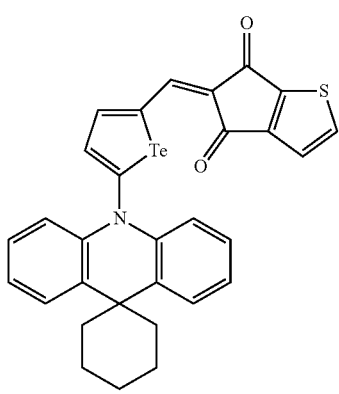

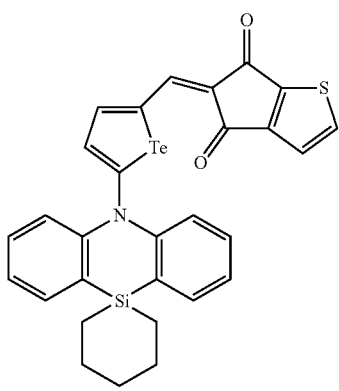

40

-continued

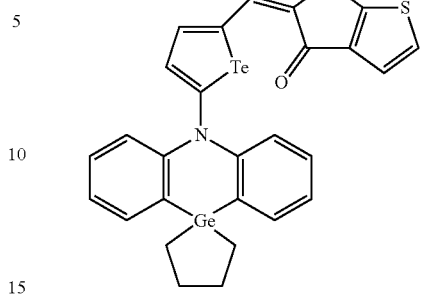

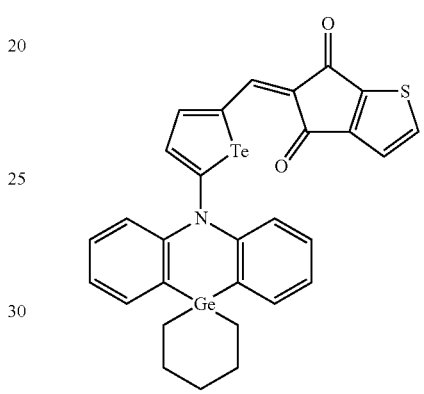

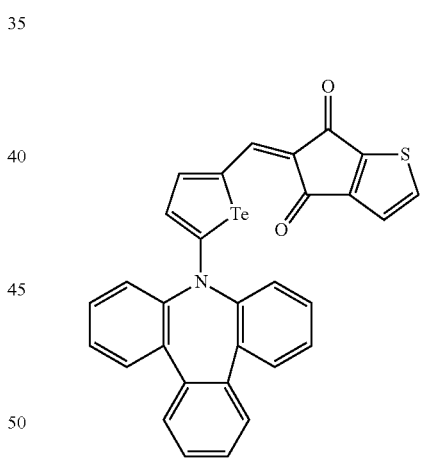

In Chemical Formula 5C, $R^e$, $R^f$, $R^g$, and $R^h$ are each independently hydrogen, a halogen, a substituted or unsubstituted C1 to C10 alkyl group, or a substituted or unsubstituted C6 to C10 aryl group, hydrogen of each ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and $R^{1a}$ and $R^{1b}$ are each independently a C1 to C6 alkyl group.

[Chemical Formula 5D]
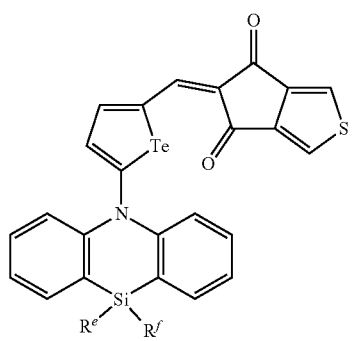
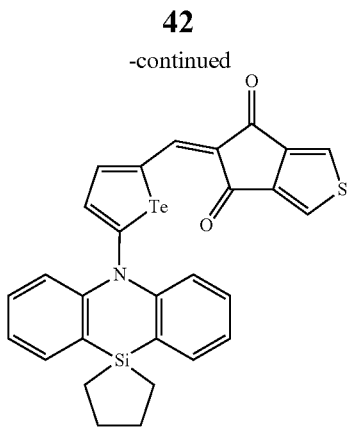
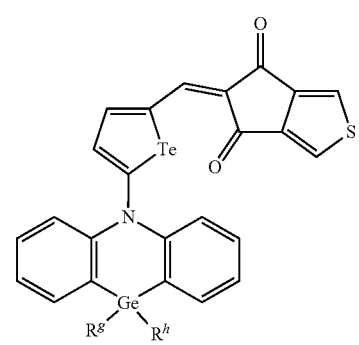
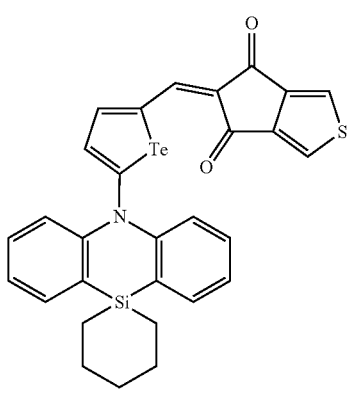
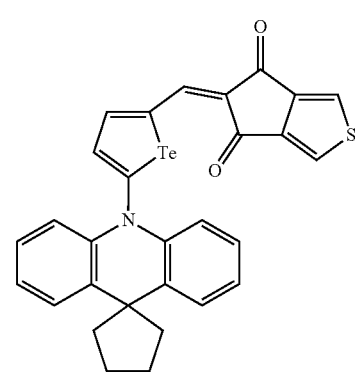
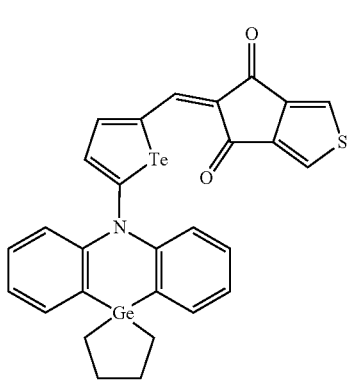
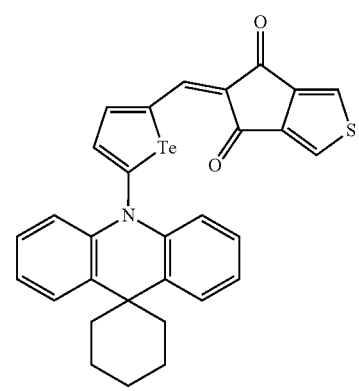
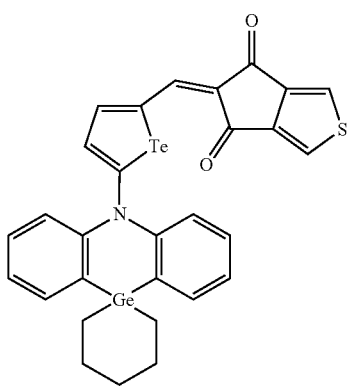

-continued

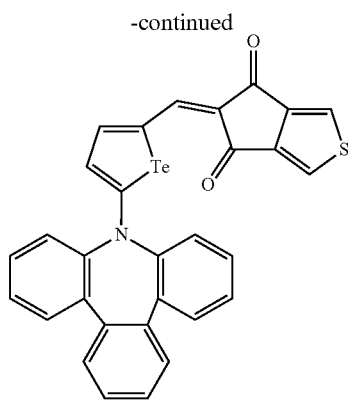

In Chemical Formula 5D, $R^e$, $R^f$, $R^g$, and $R^h$ are each independently hydrogen, a halogen, a substituted or unsubstituted C1 to C10 alkyl group, or a substituted or unsubstituted C6 to C10 aryl group, hydrogen of each ring structure may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and $R^{1a}$ and $R^{1b}$ are each independently a C1 to C6 alkyl group.

The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The donor-acceptor type material represented by Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured.

Since the compound has a higher $T_m$ than $T_s$, the compound may be formed into a thin film of high purity by the depositing process, which enables stable image sensor fabrication. In this regard, the compound may have a ($T_m$–$T_s$) of greater than or equal to about 40° C., for example greater than or equal to about 50° C., greater than or equal to about 60° C., greater than or equal to about 70° C., greater than or equal to about 80° C., greater than or equal to about 90° C., or greater than or equal to about 100° C.

The compound is a compound selectively absorbing light in a green wavelength region, and may have a maximum absorption wavelength ($\lambda_{max}$) in a wavelength region of about 520 nm to about 600 nm, for example greater than or equal to about 530 nm, greater than or equal to about 535 nm, or greater than or equal to about 540 nm and less than or equal to about 590 nm or less than or equal to about 580 nm.

The compound may exhibit a light absorption curve having a full width at half maximum (FWHM) of about 50 nm to about 130 nm, for example about 50 nm to about 120 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

In addition, a micro lens array (MLA) needs to be formed to concentrate light after manufacturing an organic photoelectric device during manufacture of an image sensor. This micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation be limited and/or prevented from the deterioration by the heat treatment. The compound may be limited and/or suppressed from the thermal vibration of molecules due to a conjugation structure (G-containing linkage structure of Chemical Formula 1) in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.2 eV to about 5.8 eV, and an energy bandgap ranging from about 1.4 eV to about 2.6 eV, the LUMO level of the compound is in a range of about 3.8 eV to about 3.2 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a bulk heterojunction (BHJ), and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 520 nm and less than or equal to about 600 nm, for example greater than or equal to about 530 nm, greater than or equal to about 535 nm, or greater than or equal to about 540 nm and less than or equal to about 590 nm or less than or equal to about 580 nm.

The active layer 30 may exhibit a light absorption curve having a relatively narrow full width at half maximum (FWHM) of about 50 nm to about 130 nm, for example about 50 nm to about 120 nm. Accordingly, the active layer 30 has high selectivity for light in a green wavelength region.

The active layer may have an absorption coefficient of greater than or equal to about $5.5\times10^4$ cm$^{-1}$, for example about $5.8\times10^4$ cm$^{-1}$ to about $10\times10^4$ cm$^{-1}$, or about $7.0\times10^4$ cm$^{-1}$ to about $10\times10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming BHJ.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 6.

[Chemical Formula 6]

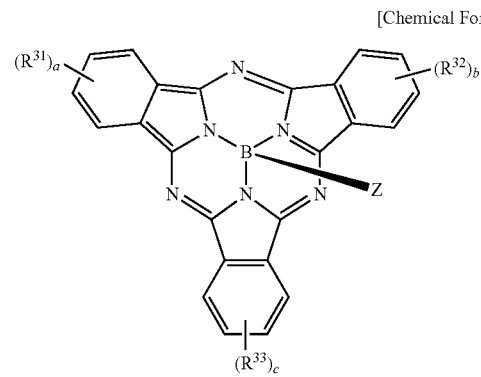

In Chemical Formula 6, $R^{31}$ to $R^{33}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers ranging from 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 7 or 8, but is not limited thereto.

[Chemical Formula 7]

[Chemical Formula 8]

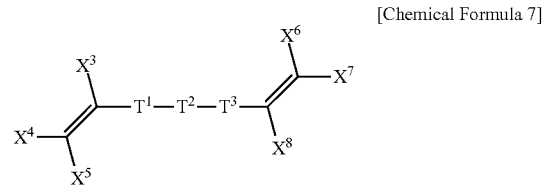

In Chemical Formulas 7 and 8, $T^1$, $T^2$, and $T^3$ are aromatic rings including substituted or unsubstituted thiophene moieties, $T^1$, $T^2$, and $T^3$ are each independently present or are fused to each other, $X^3$ to $X^8$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are each independently electron withdrawing groups.

For example, in Chemical Formula 7, at least one of $X^3$ to $X^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

[Chemical Formula 9]

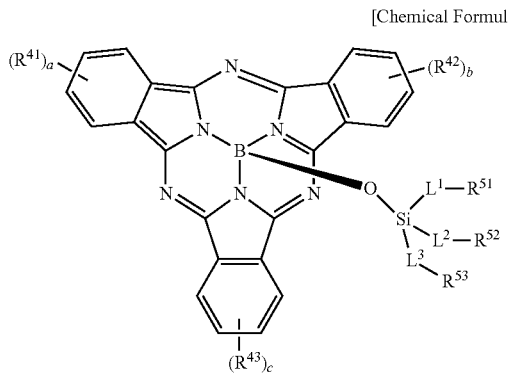

In Chemical Formula 9, $R^{41}$ to $R^{43}$ are each independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are each independently a single bond, a substituted or unsubstituted C1 to C30 alkylene group, a substituted or unsubstituted C6 to C30 arylene group, divalent substituted or unsubstituted C3 to C30 heterocyclic group, or a combination thereof, $R^{51}$ to $R^{53}$ are each independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are each independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
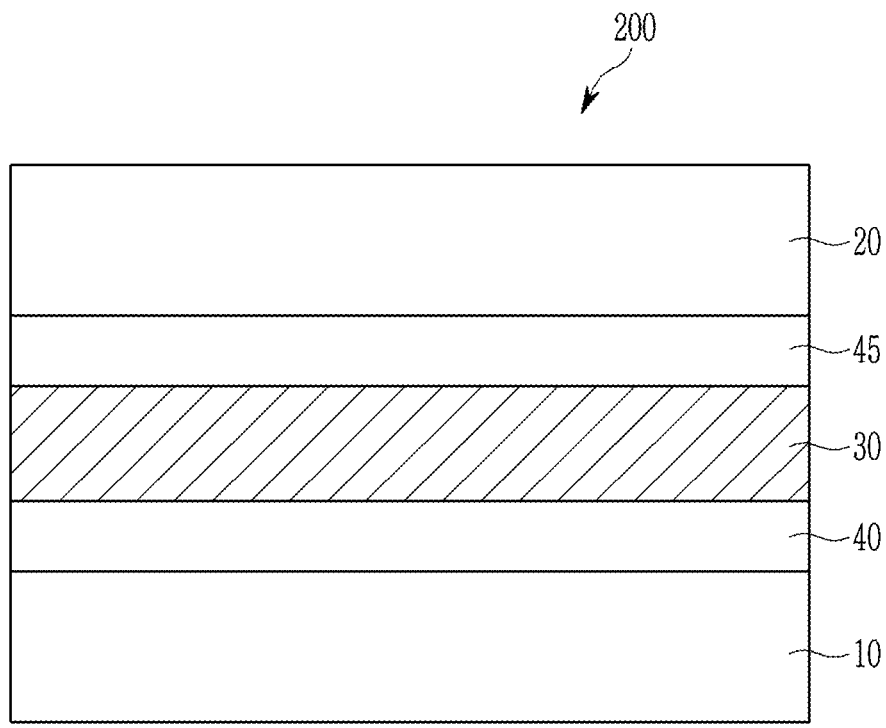
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl ($\alpha$-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
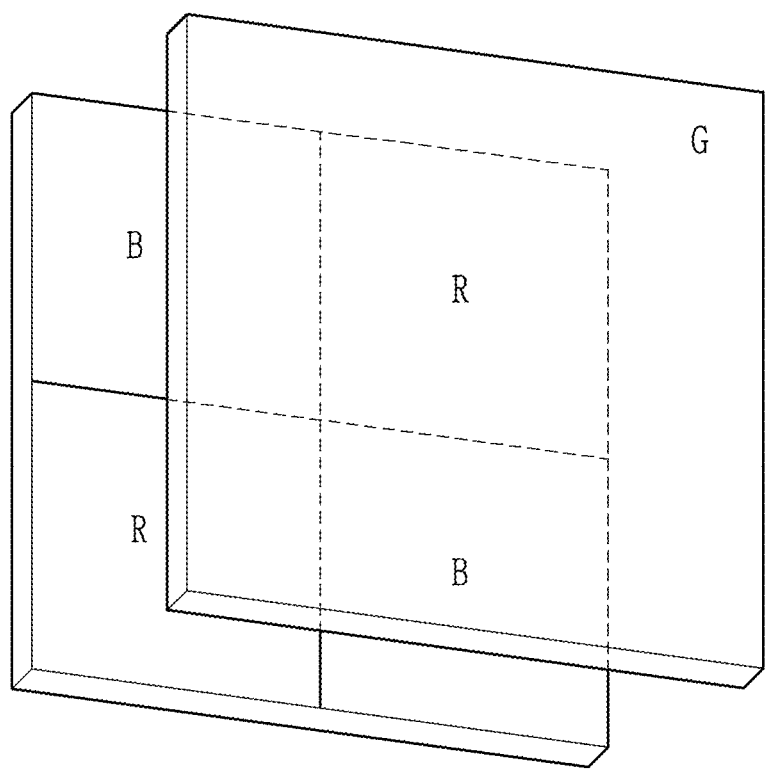
FIG. 3 is a schematic top plan view showing an organic CMOS image sensor according to an embodiment.
Figure 4:
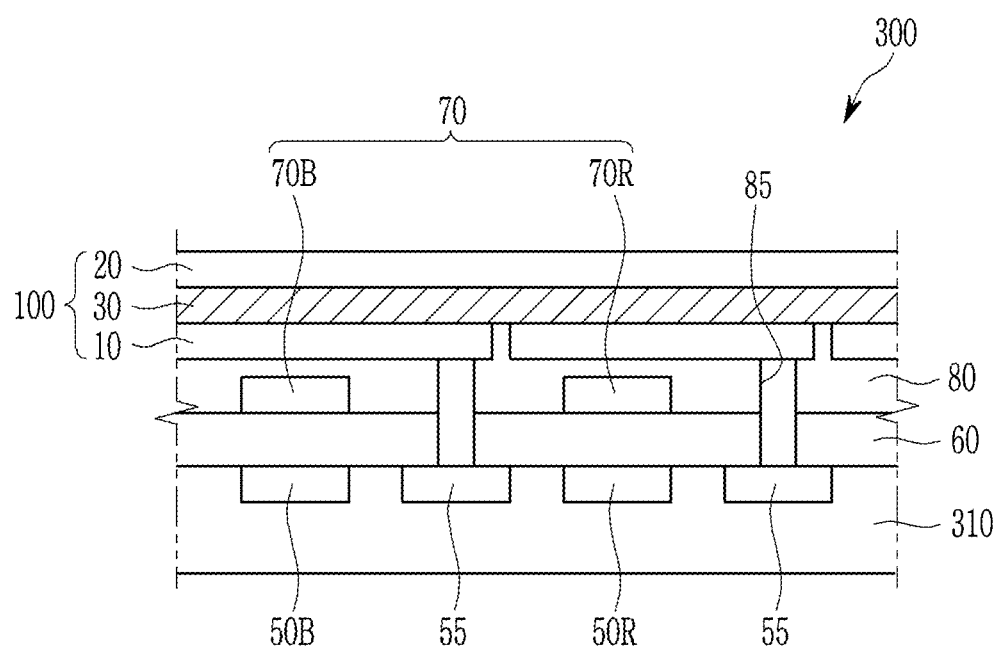
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
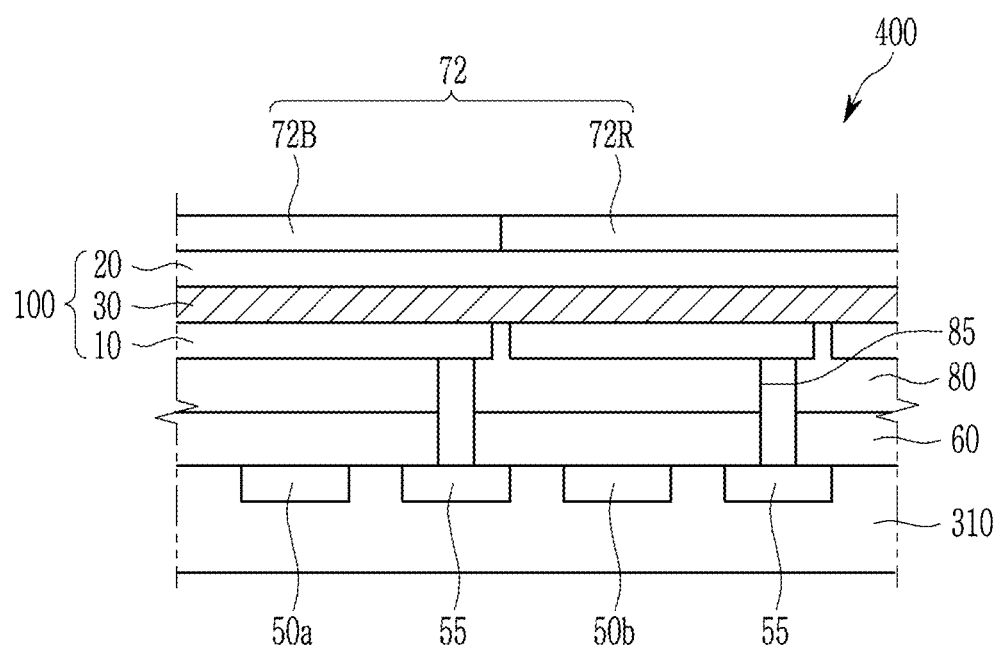
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
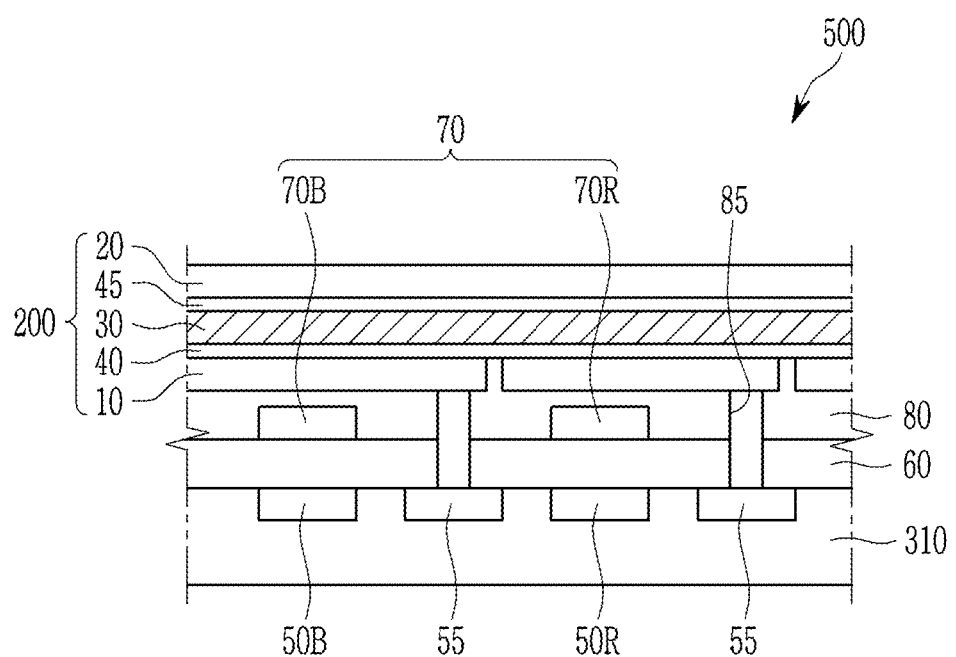
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
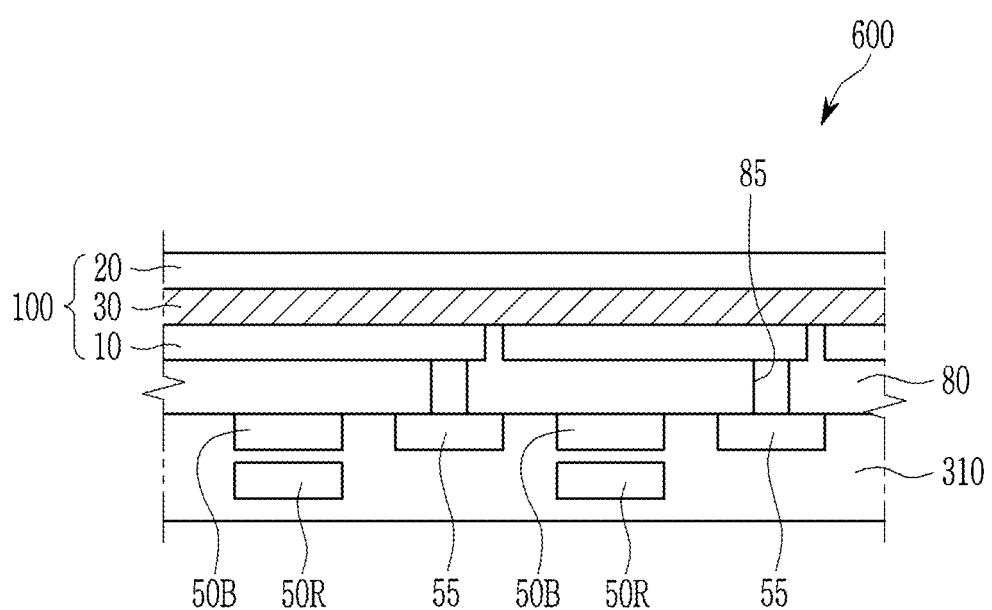
FIG. 7 is a schematic view showing an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
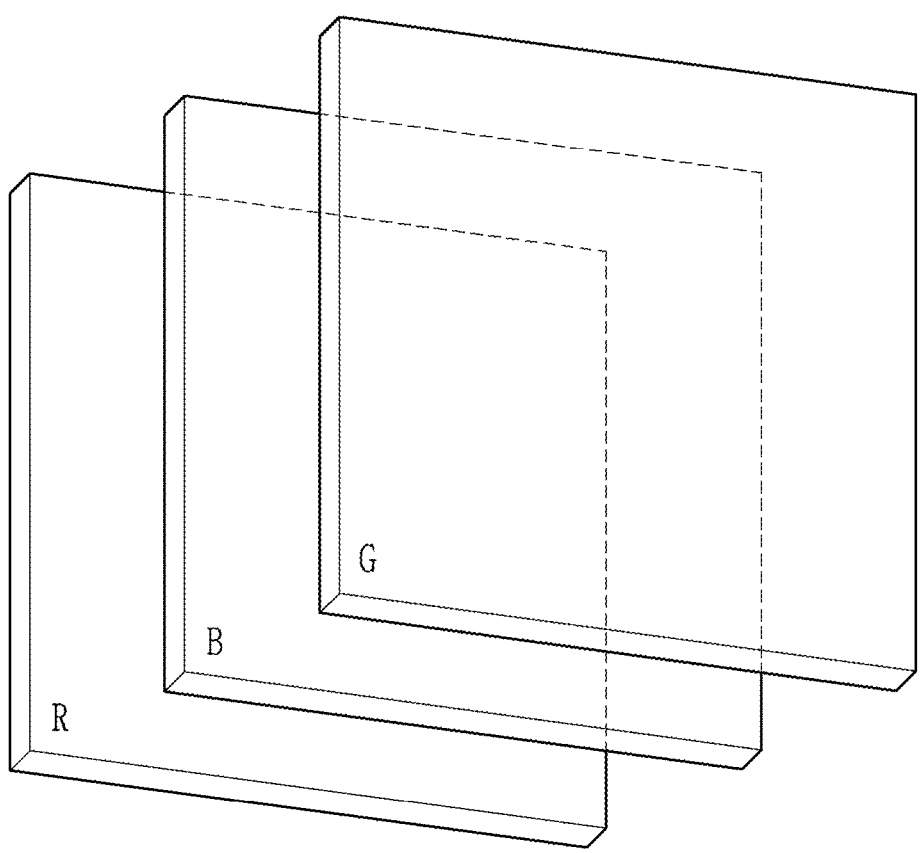
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the aforementioned photoelectric device 100 or photoelectric device 200, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the green photoelectric device (G) selectively absorbing light in a green wavelength region, the blue photoelectric device (B) selectively absorbing light in a red wavelength region, and the red photoelectric device (R) selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility ($\Delta E^*ab$) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Me., USA) but minimum illuminance expressed by lux at a ratio of 10 between signal and noise. Accordingly, the smaller the YSNR10 is, the higher sensitivity is.

On the other hand, the color reproducibility ($\Delta E^*ab$) shows a difference from standard colors in an X-Rite chart, and the $\Delta E^*ab$ is defined as a distance between two points on a L*a*b* color space by CIE (Commission International de L'Eclairage) in 1976. For example, the color difference may be calculated according to Equation 2.

$$\Delta E = \sqrt{(\Delta L^*)^2 + (\Delta a^*)^2 + (\Delta b^*)^2}$$ [Equation 2]

In Equation 2, $\Delta L^*$ denotes a change of a color coordinate L* compared with the color coordinate L* at room temperature (about 20° C. to about 25° C.), $\Delta a^*$ denotes a change of a color coordinate a* compared with the color coordinate a* at room temperature, and $\Delta b^*$ denotes a change of a color coordinate b* compared with the color coordinate b* at room temperature.

In order to manufacture an image sensor having high sensitivity and high color reproducibility, YSNR10≤100 lux at $\Delta E^*ab \leq 3$, and herein, the compound may realize YSNR10≤100 lux of sensitivity and color reproducibility at $\Delta E^*ab \leq 3$.

The image sensor may be applied to various electronic devices, for example, a mobile phone, a digital camera, and the like but is not limited thereto.

Figure 9:
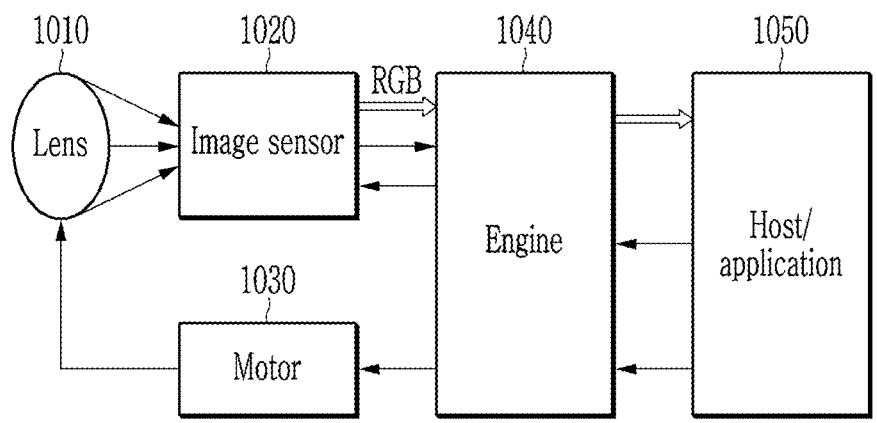
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8 of the present application.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine unit 1040. The engine 1040 may control the image sensor 1020 and the motor 1030.

The engine 1040 may be connected to a host/application 1050. In example embodiments, the motor 1030, engine 1040, and host/application 1050 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. Hereinafter, the embodiments are illustrated in more detail with reference to examples. However, these examples are non-limiting, and inventive concepts are not limited thereto.

Synthesis Example 1: Synthesis of Compound Represented by Chemical Formula 1-1 (2-((5-(10,10-dimethyldibenzo[b,e][1,4]azasilin-5(10H)-yl)tellurophen-2-yl)methylene)-1H-indene-1,3(2H)-dione)

[Chemical Formula 1-1]

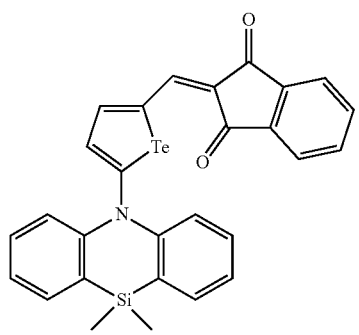

[Reaction Scheme 1-1]

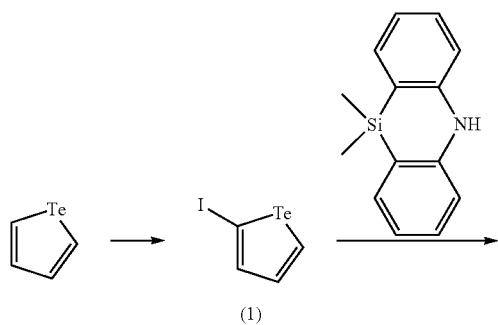

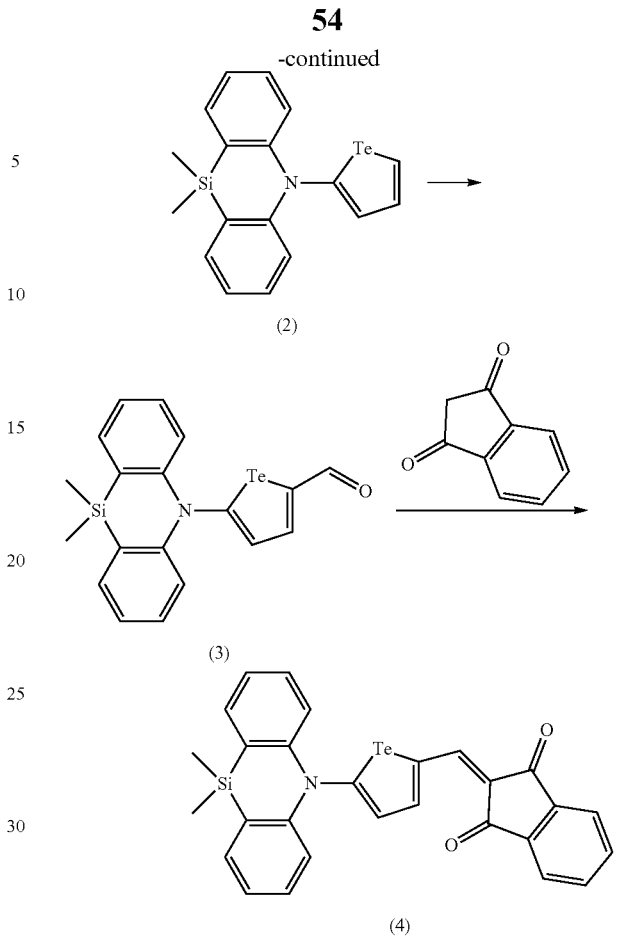

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 10.0 g (44.6 mmol) of 10,10-dimethyl-5,10-dihydrodibenzo[b,e][1,4]azasiline are heated and refluxed in 200 ml of anhydrous toluene under 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 6.8 g of 10,10-dimethyl-5-(tellurophen-2-yl)-5,10-dihydrodibenzo[b,e][1,4]azasiline (Yield: 37.8%).

(iii) Synthesis of Compound (3)

6.2 ml of phosphoryl chloride is added in a dropwise fashion to 30.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 6.8 g of Compound 2 at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.82 g of 5-(10,10-dimethyldibenzo[b,e][1,4]azasilin-5(10H)-yl)tellurophene-2-carbaldehyde (Yield: 38.8%).

(iv) Synthesis of Compound (4) Represented by Chemical Formula 1-1

2.82 g (6.54 mmol) of Compound (3) is suspended in ethanol, 1.15 g (7.85 mmol) of 1H-Indene-1,3(2H)-dione is added thereto and then, the mixture is reacted at 50° C. for 2 hours to obtain 2.20 g of a final compound represented by Chemical Formula 1-1 (Yield: 60.1%). The compound is sublimed and purified up to purity of 99.9%.

$^1$H-NMR (500 MHz, Methylene Chloride-d$_2$): δ 7.98 (s, 1H), 8.12 (m, 6H), 7.52 (m, 4H), 7.54 (m, 3H), 6.98 (d, 1H).

Synthesis Example 2: Synthesis of Compound Represented by Chemical Formula 1-2 (5-((5-(10,10-dimethyldibenzo[b,e][1,4]azasilin-5(10H)-yl)tellurophen-2-yl)methylene)-1,3-dimethyl-2-thioxodihydropyrimidine-4,6(1H,5H)-dione)

[Chemical Formula 1-2]

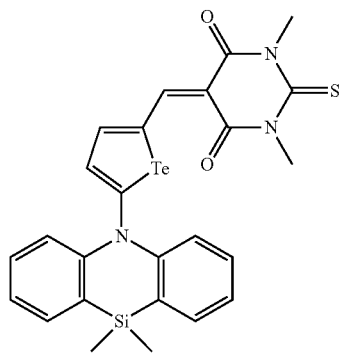

[Reaction Scheme 1-2]

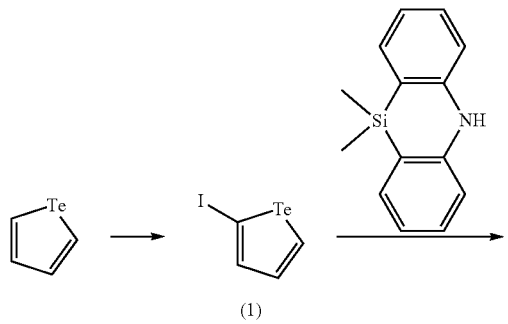

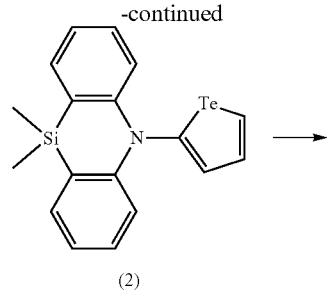

(2)

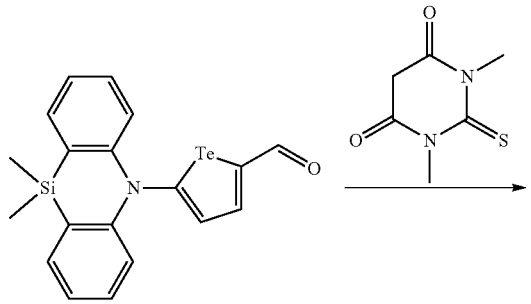

(3)

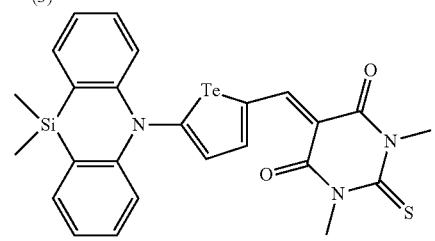

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 10.0 g (44.6 mmol) of 10,10-dimethyl-5,10-dihydrodibenzo[b,e][1,4]azasiline are heated and refluxed in 200 ml of anhydrous toluene under 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 6.8 g of 10-(selenophen-2-yl)-10H-phenoselenazine (Yield: 37.8%).

(iii) Synthesis of Compound (3)

6.2 ml of phosphoryl chloride is added in a dropwise fashion to 30.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.82 g of 5-(10,10-dimethyldibenzo[b,e][1,4]azasilin-5(10H)-yl)tellurophene-2-carbaldehyde (Yield: 38.8%).

(iv) Synthesis of Compound (4) Represented by Chemical Formula 1-2

2.82 g (6.54 mmol) of Compound (3) is suspended in ethanol, 1.35 g (7.85 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.98 g of the compound represented by Chemical Formula 1-2 (Yield: 77.8%). The compound is sublimed and purified up to purity of 99.9%.

$^1$H-NMR (500 MHz, Methylene Chloride-$d_2$): δ 8.46 (s, 1H), 8.26 (d, 1H), 7.80 (d, 2H), 7.71 (d, 2H), 7.54 (t, 2H), 7.42 (t, 2H), 6.93 (d, 1H), 3.68 (d, 6H), 0.45 (s, 6H).

Synthesis Example 3: Synthesis of Compound Represented by Chemical Formula 1-3

[Chemical Formula 1-3]

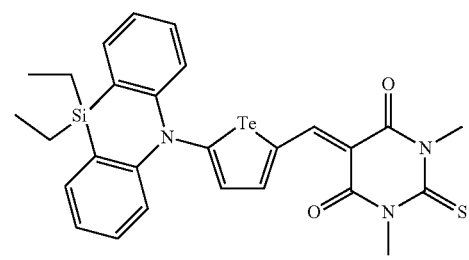

[Reaction Scheme 1-3]

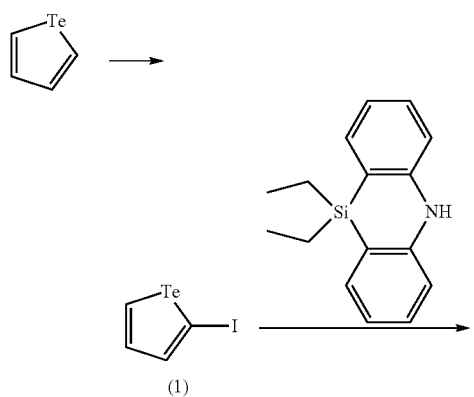

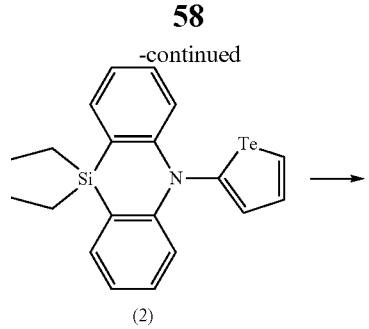

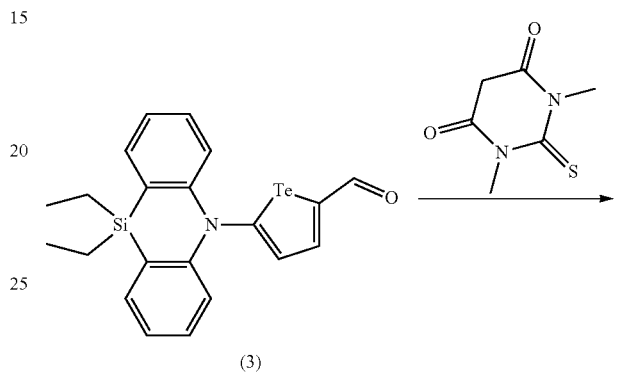

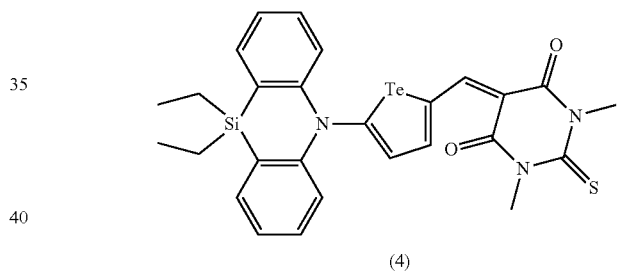

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 11.3 g (44.6 mmol) of 10,10-diethyl-5,10-dihydrodibenzo[b,e][1,4]azasiline are heated and refluxed in 200 ml of anhydrous toluene under 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 7.2 g of 10,10-diethyl-5-(tellurophen-2-yl)-5,10-dihydrodibenzo[b,e][1,4]azasiline (Yield: 37.4%).

(iii) Synthesis of Compound (3)

13.5 ml of phosphoryl chloride is added in a dropwise fashion to 34.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 7.2 g of Compound (2) at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.00 g of 5-(10,10-diethyldibenzo[b,e][1,4]azasilin-5(10H)-yl)tellurophene-2-carbaldehyde (Yield: 26.1%).

(iv) Synthesis of Compound (4) Represented by Chemical Formula 1-3

2.00 g (4.36 mmol) of Compound (3) is suspended in ethanol, 0.90 g (5.23 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.04 g of the compound represented by Chemical Formula 1-3 (Yield: 76.4%). The compound is sublimed and purified up to purity of 99.9%.

$^1$H-NMR (500 MHz, Methylene Chloride-d$_2$): δ 8.46 (s, 1H), 8.26 (d, 1H), 7.82 (d, 2H), 7.72 (d, 2H), 7.56 (t, 2H), 7.46 (t, 2H), 6.93 (d, 1H), 3.70 (d, 6H), 1.50 (t, 4H), 0.90 (s, 6H).

Synthesis Example 4: Synthesis of Compound Represented by Chemical Formula 1-4

[Chemical Formula 1-4]

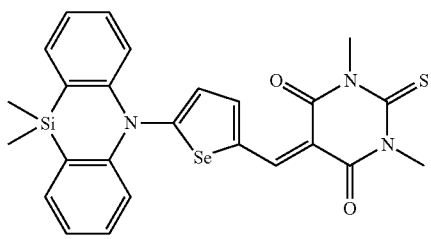

[Reaction Scheme 1-4]

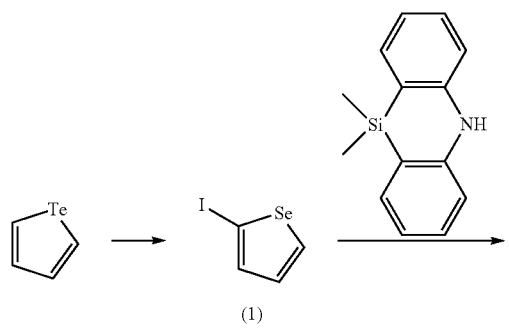

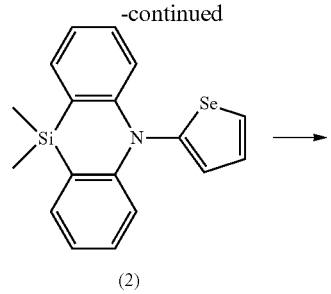

(2)

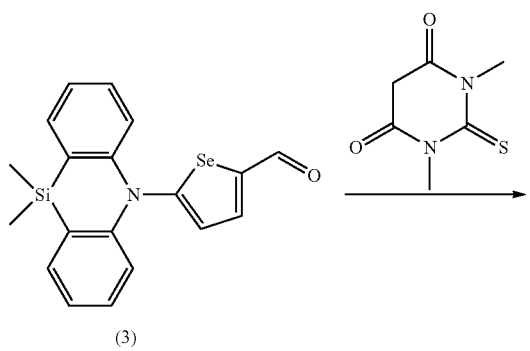

(3)

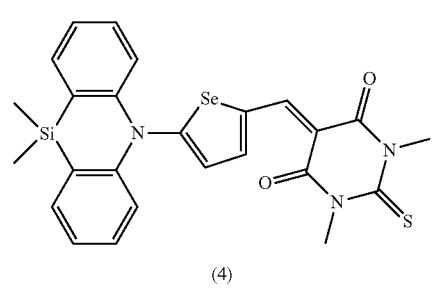

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodoselenophene and 10.0 g (44.6 mmol) of 10,10-dimethyl-5,10-dihydrodibenzo[b,e][1,4]azasiline are heated and refluxed in 200 ml of anhydrous toluene under 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 11.2 g of 10,10-dimethyl-5-(selenophen-2-yl)-5,10-dihydrodibenzo[b,e][1,4]azasiline (Yield: 49.0%).

(iii) Synthesis of Compound (3)

8.2 ml of phosphoryl chloride is added in a dropwise fashion to 38.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 11.2 g of Compound (2) at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 6.82 g of 5-(10,10-dimethyldibenzo[b,e][1,4]azasilin-5(10H)-yl)selenophene-2-carbaldehyde (Yield: 54.0%).

(iv) Synthesis of Compound (4) Represented by Chemical Formula 1-4

3.00 g (7.85 mmol) of Compound (3) is suspended in ethanol, 1.62 g (9.41 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 3.15 g of the compound represented by Chemical Formula 1-4 (Yield: 74.8%). The compound is sublimed and purified up to purity of 99.9%.

$^1$H-NMR (500 MHz, Methylene Chloride-d$_2$): δ 8.46 (s, 1H), 8.26 (d, 1H), 7.80 (d, 2H), 7.71 (d, 2H), 7.56 (t, 2H), 7.50 (t, 2H), 6.93 (d, 1H), 3.68 (d, 6H), 0.45 (s, 6H).

Synthesis Example 5: Synthesis of Compound Represented by Chemical Formula 1-5 (5-((5-(5H-spiro[dibenzo[b,e][1,4]azasiline-10,1'-silolan]-5-yl)tellurophen-2-yl)methylene)-1,3-dimethyl-2-thioxodihydropyrimidine-4,6(1H,5H)-dione)

[Chemical Formula 1-5]

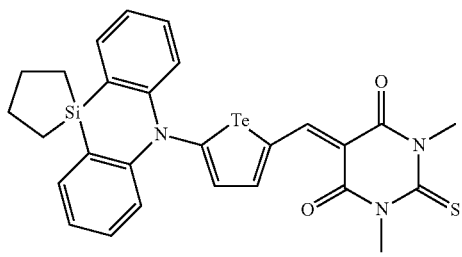

[Reaction Scheme 1-5]

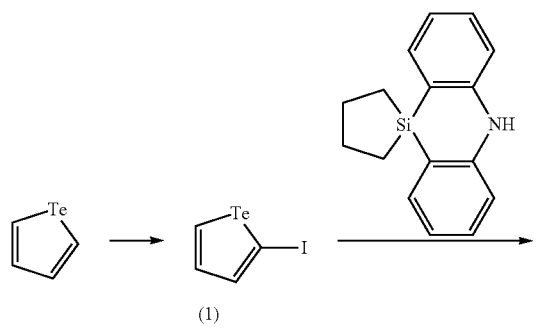

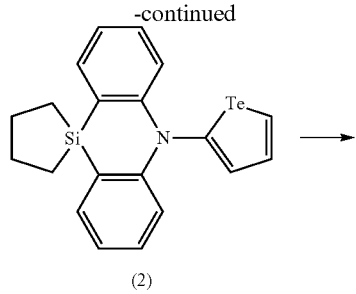

(2)

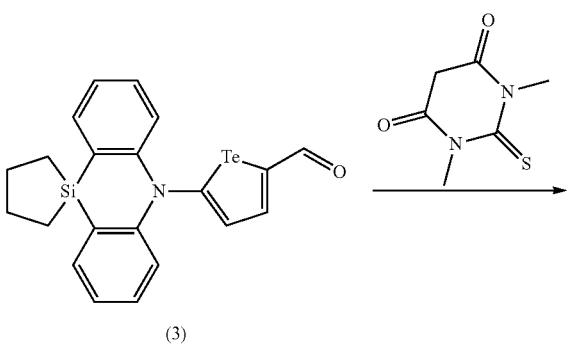

(3)

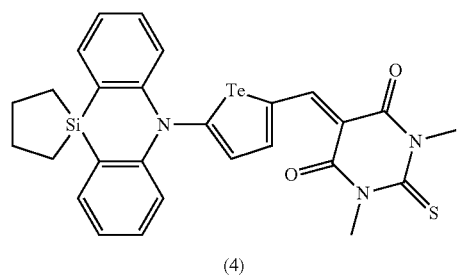

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 11.2 g (44.6 mmol) of 5H-spiro[dibenzo[b,e][1,4]azasiline-10,1'-silolane are heated and refluxed in 200 ml of anhydrous toluene under 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 6.8 g of 5-(tellurophen-2-yl)-5H-spiro[dibenzo[b,e][1,4]azasiline-10,1'-silolane (Yield: 35.5%).

(iii) Synthesis of Compound (3)

12.4 ml of phosphoryl chloride is added in a dropwise fashion to 38.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.00 g of 5-(5H-spiro[dibenzo[b,e][1,4]azasiline-10,1'-silolan]-5-yl)tellurophene-2-carbaldehyde (Yield: 27.6%).

(iv) Synthesis of Compound (4) Represented by Chemical Formula 1-5

2.00 g (4.38 mmol) of Compound (3) is suspended in ethanol, 0.90 g (5.25 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.1 g of the compound represented by Chemical Formula 1-5 (Yield: 78.5%). The compound is sublimed and purified up to purity of 99.9%.

$^1$H-NMR (500 MHz, Methylene Chloride-d$_2$): δ 8.48 (s, 1H), 8.28 (d, 1H), 7.82 (d, 2H), 7.74 (d, 2H), 7.58 (t, 2H), 7.46 (t, 2H), 6.92 (d, 1H), 3.72 (d, 6H), 1.88 (t, 8H)

Synthesis Example 6: Synthesis of Compound Represented by Chemical Formula 1-6

[Chemical Formula 1-6]

[Reaction Scheme 1-6]

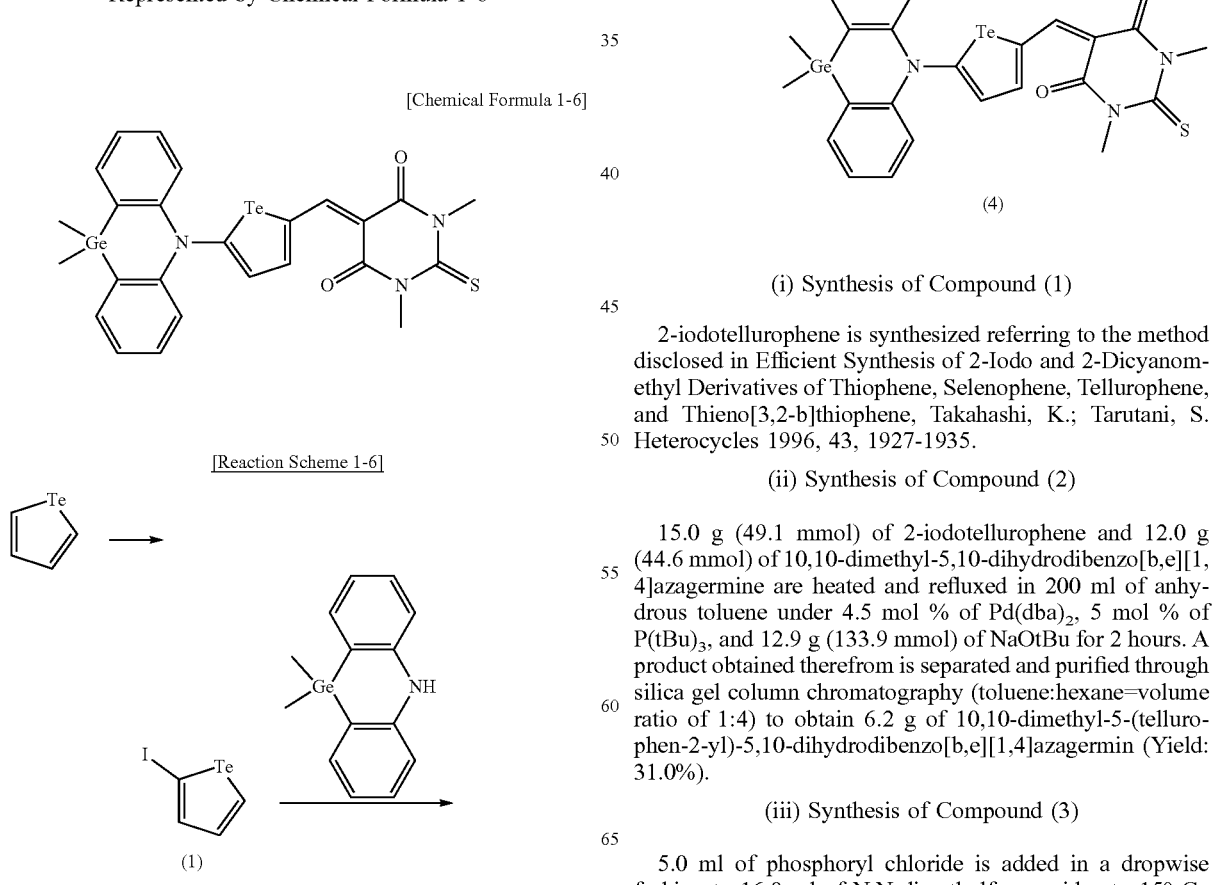

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 12.0 g (44.6 mmol) of 10,10-dimethyl-5,10-dihydrodibenzo[b,e][1,4]azagermine are heated and refluxed in 200 ml of anhydrous toluene under 4.5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=volume ratio of 1:4) to obtain 6.2 g of 10,10-dimethyl-5-(tellurophen-2-yl)-5,10-dihydrodibenzo[b,e][1,4]azagermin (Yield: 31.0%).

(iii) Synthesis of Compound (3)

5.0 ml of phosphoryl chloride is added in a dropwise fashion to 16.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 6.2 g of Compound (2) at −15° C., and the obtained mixture is stirred at room temperature for 30 minutes and concentrated under a reduced pressure. 200 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.2 g of 5-(10,10-dimethyldibenzo[b,e][1,4]azagermin-5(10H)-yl)tellurophene-2-carbaldehyde (Yield: 32.0%).

(iv) Synthesis of Compound (4) Represented by Chemical Formula 1-6

2.2 g (4.63 mmol) of Compound (3) is suspended in ethanol, 0.96 g (5.55 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.1 g of the compound represented by Chemical Formula 1-6 (Yield: 72.1%). The compound is sublimed and purified up to purity of 99.9%.

$^1$H-NMR (500 MHz, Methylene Chloride-d$_2$): δ 8.36 (s, 1H), 8.16 (d, 1H), 7.76 (d, 2H), 7.62 (d, 2H), 7.44 (t, 2H), 7.42 (t, 2H), 6.93 (d, 1H), 3.68 (d, 6H), 0.65 (s, 6H).

Reference Synthesis Example 1: Synthesis of Compound Represented by Chemical Formula 2-1

[Chemical Formula 2-1]

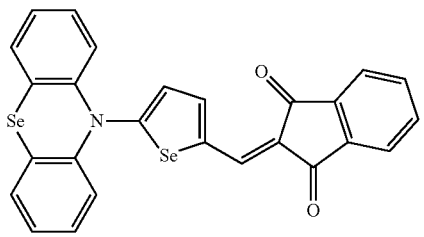

[Reaction Scheme 2-1]

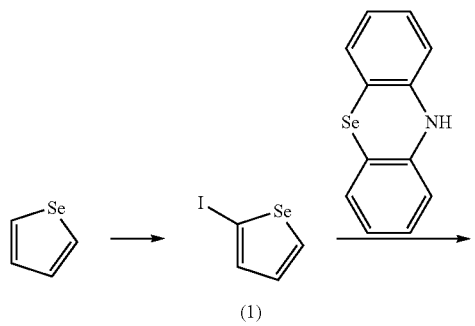

(1)

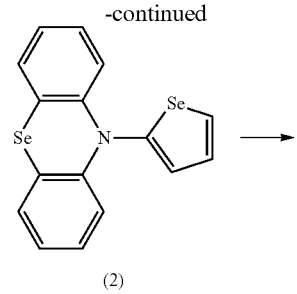

(2)

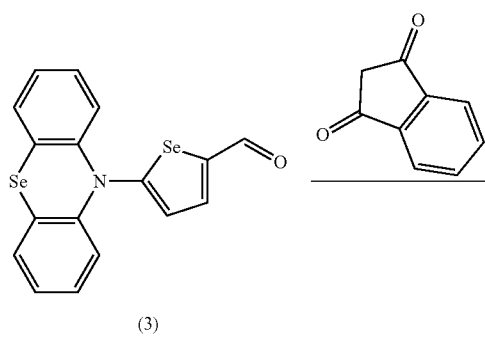

(3)

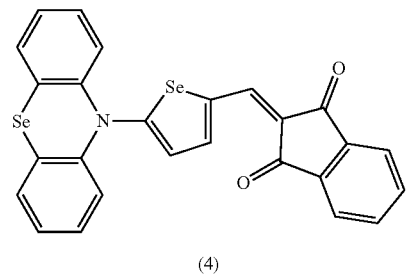

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 8.71 g (35.4 mmol) of 10H-phenoselenazine are heated and refluxed in 100 ml of anhydrous toluene under 5 mol % of Pd(dba)$_2$, 5 mol % of P(tBu)$_3$, and 10.2 g (106.15 mmol) of NaOtBu for 2 hours. A product obtained therefrom is separated and purified through silica gel column chromatography (toluene:hexane=volume ratio of 1:4) to obtain 8.2 g of 10-(selenophen-2-yl)-10H-phenoselenazine (Yield: 54.7%).

(iii) Synthesis of Compound (3)

8.0 ml of phosphoryl chloride is added in a dropwise fashion to 30.0 ml of N,N-dimethylformamide at −15° C., and the mixture is stirred at room temperature (24° C.) for 2 hours. The resultant therefrom is slowly added in a dropwise fashion to a mixture of 180 ml of dichloromethane and 8.2 g of Compound (2) at −15° C., and the obtained mixture is stirred at room temperature for 30 minutes and concentrated under a reduced pressure. 200 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 4.5 g of 5-(10H-phenoselenazin-10-yl) selenophene-2-carbaldehyde (Yield: 51.1%).

(iv) Synthesis of Compound (4) Represented by Chemical Formula 2-1

2.00 g (4.96 mmol) of Compound (3) is suspended in ethanol, 0.87 g (5.95 mmol) of 1H-Indene-1,3(2H)-dione is added thereto, and the mixture is reacted at 50° C. for 2 hours to obtain 2.0 g of the compound represented by Chemical Formula 2-1 (Yield: 75.9%). The compound is sublimed and purified up to purity of 99.9%.

$^1$H-NMR (500 MHz, Methylene Chloride-$d_2$): δ 7.87 (s, 1H), 7.72 (m, 6H), 7.49 (m, 4H), 7.42 (m, 3H), 6.82 (d, 1H).

Reference Synthesis Example 2: Synthesis of Compound Represented by Chemical Formula 2-2

[Chemical Formula 2-2]

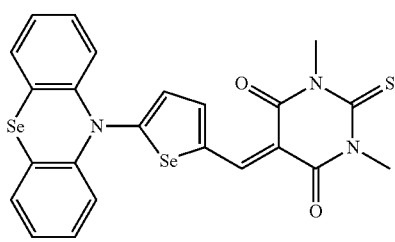

[Reaction Scheme 2-2]

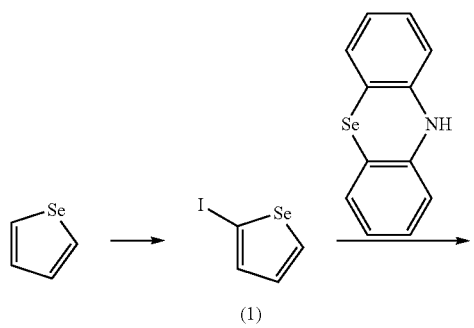

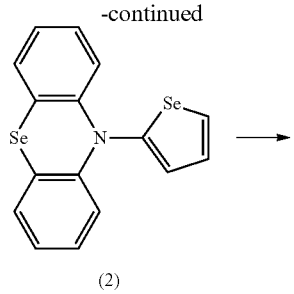

(2)

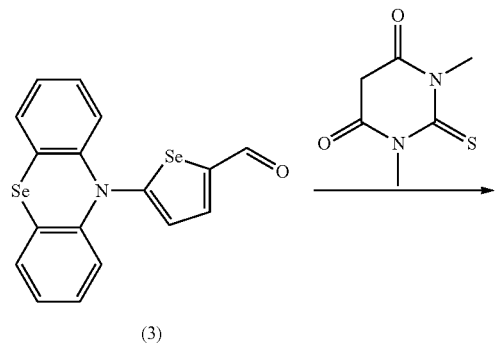

(3)

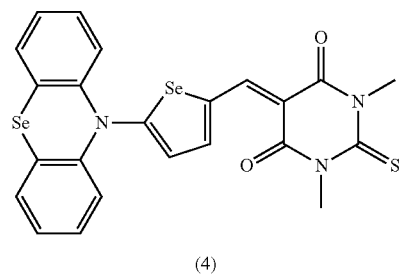

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 8.71 g (35.4 mmol) of 10H-phenoselenazine are heated and refluxed in 100 ml of anhydrous toluene under 5 mol % of Pd(dba)$_2$, 5 mol % of P(tBu)$_3$, and 10.2 g (106.15 mmol) of NaOtBu for 2 hours. A product obtained therefrom is separated and purified through silica gel column chromatography (toluene:hexane=volume ratio of 1:4) to obtain 8.2 g of 10-(selenophen-2-yl)-10H-phenoselenazine (Yield: 54.7%).

(iii) Synthesis of Compound (3)

8.0 ml of phosphoryl chloride is added in a dropwise fashion to 30.0 ml of N,N-dimethylformamide at −15° C., and the mixture is stirred at room temperature (24° C.) for 2 hours. The resultant therefrom is slowly added in a dropwise fashion to a mixture of 180 ml of dichloromethane and 8.2 g of Compound (2) at −15° C., and the obtained mixture is stirred at room temperature for 30 minutes and concentrated under a reduced pressure. 200 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane: ethylacetate=volume ratio of 4:1) to obtain 4.5 g of 5-(10H-phenoselenazin-10-yl) selenophene-2-carbaldehyde (Yield: 51.1%).

(iv) Synthesis of Compound (4) Represented by Chemical Formula 2-2

2.00 g (4.96 mmol) of Compound (3) is suspended in ethanol, 1.03 g (5.95 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.15 g of the compound represented by Chemical Formula 2-2 (Yield: 77.8%). The compound is sublimed and purified up to purity of 99.9%.

$^1$H-NMR (500 MHz, Methylene Chloride-d$_2$): δ 8.29 (s, 1H), 7.83 (d, 1H), 7.73 (d, 2H), 7.51 (d, 2H), 7.37 (t, 2H), 7.16 (t, 2H), 5.32 (d, 1H), 3.67 (d, 6H).

Reference Synthesis Example 3: Synthesis of Compound Represented by Chemical Formula 2-3 (5-((5-(10H-phenoselenazin-10-yl)tellurophen-2-yl)methylene)-1,3-dimethyl-2-thioxodihydropyrimidine-4,6(1H,5H)-dione)

[Chemical Formula 2-3]

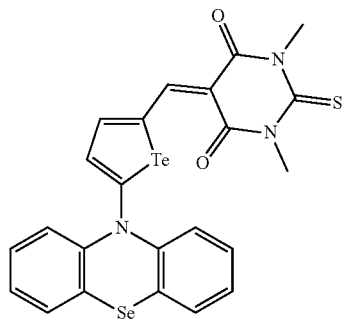

[Reaction Scheme 2-3]

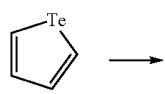

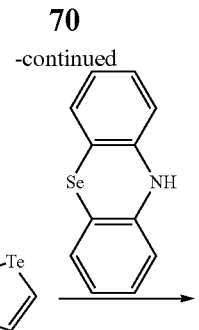

(1)

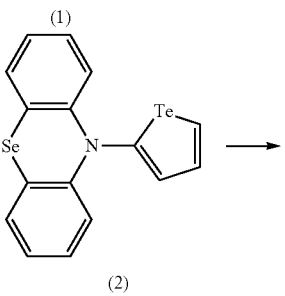

(2)

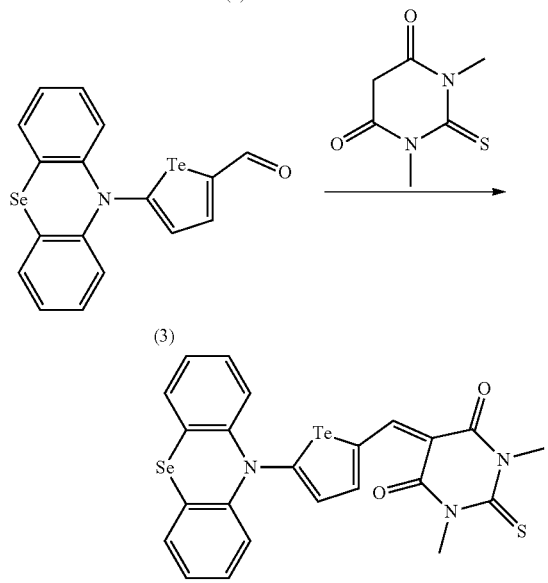

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 6.17 g (25.2 mmol) of 10H-phenoselenazine are heated and refluxed in 100 ml of anhydrous toluene under 5 mol % of Pd(dba)$_2$, 5 mol % of P(tBu)$_3$, and 2.66 g (27.7 mmol) of NaOtBu for 2 hours. A product therefrom is separated and purified through silica gel column chromatography (toluene: hexane=volume ratio of 1:4) to obtain 4.25 g of 10-(tellurophen-2-yl)-10H-phenoselenazine (Yield: 19.6%).

(iii) Synthesis of Compound (3)

1.84 ml of phosphoryl chloride is added in a dropwise fashion to 6.0 ml of N,N-dimethylformamide at −15° C., and the mixture is stirred at room temperature (24° C.) for 2 hours. The resultant therefrom is slowly added in a dropwise fashion to a mixture of 180 ml of dichloromethane and 2.10 g of Compound (2) at −15° C., and the obtained mixture is stirred at room temperature for 30 minutes and concentrated under a reduced pressure. 100 ml of water is added thereto, an aqueous sodium hydroxide solution is added thereto until pH becomes 14, and the obtained mixture is stirred at room temperature (24° C.) for 2 hours. An organic layer is extracted therefrom by using dichloromethane and washed with an aqueous sodium chloride solution and then, dried by adding magnesium sulfate anhydrous thereto. A product therefrom is separated and purified through silica gel column chromatography (hexane:ethylacetate=volume ratio of 4:1) to obtain 2.50 g of 5-(10H-phenoselenazin-10-yl)telluro-phene-2-carbaldehyde (Yield: 53.6%).

(iv) Synthesis of Compound (4) Represented by Chemical Formula 2-3

2.50 g (4.21 mmol) of Compound (3) is suspended in ethanol, 0.87 g (5.05 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 1.76 g of the compound represented by Chemical Formula 2-3 (Yield: 69.1%). The compound is sublimed and purified up to purity of 99.9%.

$^1$H-NMR (500 MHz, Methylene Chloride-d$_2$): δ 8.29 (s, 1H), 7.83 (d, 1H), 7.73 (d, 2H), 7.51 (d, 2H), 7.37 (t, 2H), 6.99 (t, 2H), 5.32 (d, 1H), 3.67 (d, 6H).

Example 1: Manufacture of Photoelectric Device

An about 150 nm-thick anode is formed by sputtering ITO on a glass substrate, and a 100 nm-thick active layer is formed thereon by code positing a compound represented by Chemical Formula 1-1 according to Synthesis Example 1 (p-type semiconductor compound) and C60 (n-type semiconductor compound) in a volume ratio of 1:1. Subsequently, a 10 nm-thick molybdenum oxide (MoO$_x$, 0<x≤3) thin film is formed thereon as a charge auxiliary layer. On the molybdenum oxide thin film, a 7 nm-thick cathode is formed by sputtering ITO, manufacturing an organic photoelectric device.

Examples 2 to 6: Manufacture of Photoelectric Device

Photoelectric devices according to Examples 2 to 6 are manufactured according to the same method as Example 1 except that the compounds according to Synthesis Examples 2 to 6 are used respectively instead of the compound according to Synthesis Example 1.

Reference Examples 1 to 3: Manufacture of Photoelectric Device

Photoelectric devices according to Reference Examples 1 to 3 are manufactured according to the same method as Example 1 except that the compounds according to Reference Synthesis Example 1 to 5 are used respectively instead of the compound according to Synthesis Example 1.

Evaluation 1: Light Absorption Characteristics of Compounds

Light absorption characteristics (maximum absorption wavelength and full width at half maximum (FWHM)) of the compounds according to Synthesis Examples 1 to 6 and Reference Synthesis Example 1 depending on a wavelength are evaluated. Light absorption characteristics in an ultraviolet (UV)-visible (UV-Vis) region of each photoelectric device according to Examples 1 to 6 and Reference Synthesis Example 1 including each compound according to Synthesis Examples 1 to 6 and Reference Synthesis Example 1 are evaluated using Cary 5000 UV Spectroscopy (Varian Medical Systems). The results are shown in Table 1.

TABLE 1

| Example | Compound structure | $\lambda_{max}$ (nm) | FWHM (nm) |
|---|---|---|---|
| Example 1 | Chemical Formula 1-1 | 549 | 97 |
| Example 2 | Chemical Formula 1-2 | 545 | 96 |
| Example 3 | Chemical Formula 1-3 | 545 | 96 |
| Example 4 | Chemical Formula 1-4 | 530 | 98 |
| Example 5 | Chemical Formula 1-5 | 545 | 97 |
| Example 6 | Chemical Formula 1-6 | 545 | 96 |
| Reference Example 1 | Chemical Formula 2-1 | 515 | 96 |

Referring to Table 1, the photoelectric devices according to Examples 1 to 6 exhibit a maximum absorption wavelength ($\lambda_{max}$) at greater than or equal to 530 nm and a low full width at half maximum (FWHM). Accordingly, the photoelectric devices according to Examples 1 to 6 have high wavelength selectivity in a green wavelength region. On the contrary, the photoelectric device according to Reference Example 1 exhibits a low maximum absorption wavelength of 515 nm.

Evaluation 2: Thermal Stability of Compounds

In order to evaluate thermal stability of the compounds according to Synthesis Examples 1 to 6, a deposition temperature ($T_{S10}$) where 10 wt % of each compound at 10 Pa is decomposed and a deposition temperature ($T_{S50}$) where 50 wt % of each compound at 10 Pa is decomposed are measured. The deposition temperatures are measured using a thermal gravimetric analysis (TGA) method. The results of Synthesis Examples 1, 2, 5, and 6 are shown in Table 2.

TABLE 2

| Synthesis Examples | Chemical Formula | $T_d$ (° C.) | $T_{s10}$ (10 wt %, 10 Pa) (° C.) | $T_{s50}$ (50 wt %, 10 Pa) (° C.) | $\Delta T$ ($T_m - T_{s10}$) (° C.) |
|---|---|---|---|---|---|
| Synthesis Example 1 | Chemical Formula 1-1 | 345 | 235 | 265 | 110 |
| Synthesis Example 2 | Chemical Formula 1-2 | 357 | 243 | 271 | 114 |
| Synthesis Example 5 | Chemical Formula 1-5 | 360 | 240 | 264 | 120 |
| Synthesis Example 6 | Chemical Formula 1-6 | 363 | 240 | 264 | 123 |
| Reference Synthesis Example 1 | Chemical Formula 2-1 | 325 | 231 | 265 | 90 |
| Reference Synthesis Example 2 | Chemical Formula 2-2 | 294 | 242 | 270 | 52 |
| Reference Synthesis Example 3 | Chemical Formula 2-3 | 281 | 248 | 280 | 33 |

When a compound has a lower melting point than a deposition temperature during the vacuum deposition, the compound may be decomposed and simultaneously gasified and thus fails in being formed into a film. Accordingly, the melting point of a compound may desirably be higher than the deposition temperature. Referring to Table 2, the compounds according to Synthesis Examples 1, 2, 5, and 6 exhibit greater than or equal to 110° C. of a large difference (ΔT) between the melting point and deposition temperature. On the contrary, the compounds according to Reference Synthesis Examples 1 to 3 exhibit low ΔT compared with the compounds of Synthesis Examples 1, 2, 5, and 6. Accordingly, the compounds according to Synthesis Examples 1, 2, 5, and 6 may sufficiently secure process stability compared with the compounds according to Reference Synthesis Examples 1 to 3.

Evaluation 4: External Quantum Efficiency (EQE) of Photoelectric Device

External quantum efficiency (EQE) of the photoelectric devices according to Examples 1 to 6 and Reference Examples 1 to 3 is evaluated. The external quantum efficiency (EQE) is measured by using an IPCE measurement system (McScience Inc., Korea). The EQE is measured at a wavelength ranging from about 350 nm to about 750 nm by calibrating IPCE measurement system with the Si photodiode (Hamamatsu Photonics K.K., Japan) and respectively mounting the organic photoelectric devices according to Examples 1 to 6 and Reference Examples 1 to 3.

In addition, after the photoelectric devices according to Examples 1 to 6 and Reference Examples 1 to 3 are heat-treated at 160° C. for 3 hours, at 170° C. for 3 hours, and at 180° C. for 3 hours, EQE is measured at a wavelength ranging from about 350 nm to about 750 nm using the measurement system.

Of them, the results of the photoelectric devices according to Examples 1, 2, 5, and 6 and Reference Example 1 are shown in Table 3. In Table 3, the external quantum efficiency is measured at a maximum light absorption wavelength when a −3V voltage is applied thereto.

TABLE 3

| Example | Compound structure | EQE (%) at −3 V | | | |
| --- | --- | --- | --- | --- | --- |
| | | No heat treatment | 160° C. (3 h) | 170° C. (3 h) | 180° C. (3 h) |
| Example 1 | Chemical Formula 1-1 | 65 | 65 | 65 | 63 |
| Example 2 | Chemical Formula 1-2 | 66 | 66 | 65 | 65 |
| Example 5 | Chemical Formula 1-5 | 62 | 62 | 61 | 60 |
| Example 6 | Chemical Formula 1-6 | 62 | 63 | 64 | 62 |
| Reference Example 1 | Chemical Formula 2-1 | 56 | 57 | 50 | 42 |

Referring to Table 3, the photoelectric devices according to Examples 1, 2, 5, and 6 show excellent external quantum efficiency after high-temperature heat treatment as well as at room temperature (no heat treatment).

In addition, after the photoelectric devices according to Example 2, Example 6, and Reference Example 1 are heat-treated at 190° C. for 3 hours, at 200° C. for 3 hours, and at 210° C. for 3 hours, EQE is measured at a wavelength ranging from about 350 nm to about 750 nm using the measurement system. The results are shown in Table 4.

TABLE 4

| Examples | EQE (%) at −3 V | | |
| --- | --- | --- | --- |
| | 190° C. (3 h) | 200° C. (3 h) | 210° C. (3 h) |
| Example 2 | 65 | 61 | 56 |
| Example 6 | 62 | 62 | 61 |
| Reference Example 1 | 40 | fail | fail |

Referring to Table 4, the photoelectric devices according to Examples 2 and 6 exhibit satisfactory external quantum efficiency at a high temperature of greater than or equal to 190° C. compared with the photoelectric device according to Reference Example 1. On the contrary, as the photoelectric device according to Reference Example 1 is discolored at greater than or equal to 200° C., a short circuit occurs, and accordingly, EQE thereof cannot be measured.

Evaluation 5: Dark Current of Photoelectric Device

Dark current (DC) of the photoelectric device according to Examples 1 to 6 and Reference Examples 1 to 3 is evaluated. The dark current is measured by using an IPCE measurement system (McScience Inc., Korea). The dark current is measured at a wavelength ranging from about 350 nm to about 750 nm by calibrating IPCE measurement system with the Si photodiode (Hamamatsu Photonics K.K., Japan) and respectively mounting the organic photoelectric devices according to Examples 1 to 6 and Reference Examples 1 to 3.

In addition, after the photoelectric devices according to Examples 1 to 6 and Reference Examples 1 to 3 are heat-treated at 170° C. for 3 hours, at 180° C. for 3 hours, and at 190° C. for 3 hours, dark currents are measured at a wavelength ranging from about 350 nm to about 750 nm using the measurement system.

Of them, the results of Example 2, Example 6, and Reference Example 1 are shown in Table 7. In Table 5, the dark current is measured at a maximum light absorption wavelength when a −3V voltage is applied thereto.

TABLE 5

| Examples | DC (h/s/μm²) | | |
| --- | --- | --- | --- |
| | 170° C. (3 h) | 180° C. (3 h) | 190° C. (3 h) |
| Example 2 | 47 | <0.5 | 10 |
| Example 6 | 8 | 73 | 128 |
| Reference Example 1 | 900 | Fail | Fail |

Referring to Table 5, the photoelectric devices according to Examples 2 and 6 may exhibit a dark current after the heat treatment at a high temperature compared with the photoelectric device according to Reference Example 1. On the contrary, as the photoelectric device according to Reference Example 1 is discolored at greater than or equal to 180° C., a short circuit occurs, and accordingly, a dark current thereof cannot be measured.

Evaluation 6: Response Time of Photoelectric Device

The response times (lag times) of the photoelectric devices according to Examples 1 to 6 and Reference Examples 1 to 3 are evaluated. The response time is measured by using incident LED light having a middle wavelength of 530 nm from an upper electrode (a cathode), applying it with electric intensity of 3 V/100 nm to the photoelectric devices according to Examples 1 to 6 and Reference Examples 1 to 3, and measuring an after-image current 0.1 second later after turning off the LED light.

In addition, in order to evaluate thermal stability of the photoelectric devices according to Examples 1 to 6 and Reference Examples 1 to 3, after the photoelectric devices according to Examples 1 to 6 and Reference Examples 1 to 3 are heat-treated at 170° C. for 3 hours, at 180° C. for 3 hours, at 190° C. for 3 hours, and at 200° C. for 3 hours, response times after being allowed at a high temperature are measured according to the same method as described above.

Of them, the results of Example 2, Example 6, and Reference Example 1 are shown in Table 6.

TABLE 6

| | Lag time @ 10 μW/cm² (ms) | | | |
|---|---|---|---|---|
| | 170° C. (3 h) | 180° C. (3 h) | 190° C. (3 h) | 200° C. (3 h) |
| Example 2 | 97 | 89 | 51 | 79 |
| Example 6 | 170 | 146 | 146 | 130 |
| Reference Example 1 | 238 | 556 | fail | fail |

Referring to Table 6, the photoelectric devices according to Examples 2 and 6 exhibit a fast response speed after the heat treatment at a high temperature. On the contrary, as the photoelectric device according to Reference Example 1 is discolored at greater than or equal to 190° C., a short circuit occurs, and accordingly, response time thereof cannot be measured.

Evaluation 7: Sensitivity (YSNR10) of Image Sensor

The photoelectric devices according to Examples 1 to 6 and Reference Examples 1 to 3 are respectively disposed to manufacture image sensors to have the structure of an organic photoelectric device 100 of an image sensor 300 as shown in FIG. 4.

YSNR10 and a color difference ΔE*ab from 24 colors of a Macbeth chart are measured by taking a photo of an 18% gray patch of the Macbeth chart under a light source of D-65.

Herein, lens has an F value of 2.8 and transmittance of 80%, and interference-type lens are used for an infrared ray cut filter. A pixel size of the image sensors is 1.4 μm, and a frame rate of the image sensors is 15 fps.

The YSNR10 is obtained in a method described in Juha Alakarhu's "Image Sensors and Image Quality in Mobile Phones" printed in the outline of 2007 International Image Sensor Workshop (Ogunquit Me., USA). The YSNR10 (luminance) is obtained at ΔE*ab=3 by compensating a color with CCM (Color Correction Matrix). After allowing the image sensors to stand at 160° C. for 3 hours, YSNR10 at ΔE*ab=3 is measured. The results of Example 2, Example 6, and Reference Example 1 are shown in Table 2.

TABLE 7

| | YSNR10 (lux) | YSNR10 (160° C., 3 h) (lux) |
|---|---|---|
| Example 2 | 94 | 87 |
| Example 6 | 95 | 80 |
| Reference Example 1 | 126 | 115 |

Referring to Table 7, each image sensor including the photoelectric devices according to Examples 2 and 6 respectively exhibits low YSNR10 of 94 and 95 at ΔE*ab=3 color-calibrated with CCM (Color Correction Matrix) and accordingly, may be applied as a high sensitivity image sensor in a pixel of considerably high image quality of 1.4 μm. In addition, after the heat treatment at 160° C. for 3 hours, YSNR10 of 87 and 89 is respectively obtained, and accordingly, the devices are not deteriorated after the heat treatment. On the contrary, an image sensor including the photoelectric device according to Reference Example 1 exhibits YSNR10 of 126 and after the heat treatment, YSNR10 of 115.

While this disclosure has been described in connection with what is presently considered to be practical example embodiments, it is to be understood that inventive concepts are not limited to the disclosed embodiments. On the contrary, inventive concepts are intended to cover various modifications and equivalent arrangements included within the spirit and scope of the appended claims.

What is claimed is:

1. A compound represented by Chemical Formula 1:

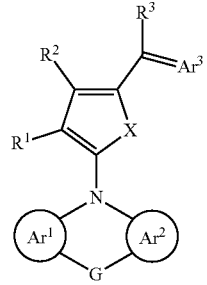

[Chemical Formula 1]

wherein, in Chemical Formula 1,

Ar¹ and Ar² are each independently a substituted or unsubstituted C6 to C30 arene group, a substituted or unsubstituted C3 to C30 heteroarene group, or a condensed ring thereof, Ar³ is a substituted or unsubstituted hydrocarbon cyclic group having two carbonyl groups, a substituted or unsubstituted heterocyclic group having two carbonyl groups, or a fused ring thereof, X is Se, Te, or SiR$^a$R$^b$ (wherein R$^a$ and R$^b$ are each independently hydrogen, a halogen, a substituted or unsubstituted C1 to C10 alkyl group, or a substituted or unsubstituted C6 to C10 aryl group), R¹ to R³ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein R¹ and R² are each independently present or linked with each other to provide a ring, G is —SiR$^e$R$^f$—, —GeR$^g$R$^h$—, —CR$^{cc}$R$^{dd}$—, —SiR$^{ee}$R$^{ff}$—, —GeR$^{gg}$R$^{hh}$—, —(C(R$^{ii}$)=C(R$^{jj}$))—, or G'(CR$^x$R$^y$)$_n$, wherein R$^e$, R$^f$, R$^g$, and R$^h$ are each independently hydrogen, a halogen, a substituted or unsubstituted C1 to C10 alkyl group, or a substituted or unsubstituted C6 to C10 aryl group, wherein the pairs of R$^{cc}$ and R$^{dd}$, R$^{ee}$ and R$^{ff}$, R$^{gg}$ and R$^{hh}$, and R$^{ii}$ and R$^{jj}$ are linked with each other to provide a ring, wherein, in G'(C$R^xR^y$)$_n$,
G' is —C—, —Si—, —Ge—, or —C≡C—,
$R^x$ and $R^y$ are each independently hydrogen, a halogen, a substituted or unsubstituted C1 to C10 alkyl group, or a substituted or unsubstituted C6 to C10 aryl group, and
n is an integer of 3 to 8, and
a melting point ($T_m$) and a deposition temperature ($T_s$) of the compound satisfy Equation 1:

$$T_m - T_s \geq 40° \text{ C.} \qquad \text{[Equation 1]}$$

2. The compound of claim 1, wherein the ring provided by linking $R^{cc}$ and $R^{dd}$, $R^{ee}$ and $R^{ff}$, $R^{gg}$ and $R^{hh}$, or $R^{ii}$ and $R^{jj}$ has a spiro structure or a fused ring structure.

3. The compound of claim 1, wherein the compound represented by Chemical Formula 1 is a compound represented by Chemical Formula 1A:

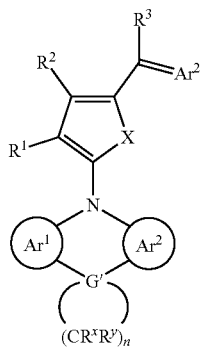

[Chemical Formula 1A]

wherein, in Chemical Formula 1A,
$Ar^1$, $Ar^2$, $Ar^3$, X, and $R^1$ to $R^3$ are the same as in Chemical Formula 1,
G' is —C—, —Si—, —Ge—, or —C≡C—,
$R^x$ and $R^y$ are each independently hydrogen, a halogen, a substituted or unsubstituted C1 to C10 alkyl group, or a substituted or unsubstituted C6 to C10 aryl group, and
n is an integer of 3 to 8.

4. The compound of claim 3, wherein in Chemical Formula 1A, at least one non-adjacent C($R^xR^y$) is replaced by at least one of —N—, —$NR^a$— (wherein $R^a$ is hydrogen, a halogen, a substituted or unsubstituted C1 to C10 alkyl group, or a substituted or unsubstituted C6 to C10 aryl group), —O—, —S—, —Se—, and —Te—.

5. The compound of claim 1, wherein in Chemical Formula 1, $Ar^3$ is a cyclic group represented by Chemical Formula 2A:

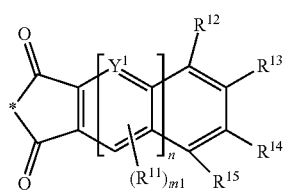

[Chemical Formula 2A]

wherein, in Chemical Formula 2A,
$Y^1$ is N or $CR^a$ (wherein $R^a$ is hydrogen, deuterium, or a substituted or unsubstituted C1 to C10 alkyl group),
$R^{11}$, $R^{12}$, $R^{13}$, $R^{14}$, and $R^{15}$ are hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof,
or a pair of $R^{12}$ and $R^{13}$ or a pair of $R^{14}$ and $R^{15}$ is each independently linked with each other to provide a fused aromatic ring,
m1 is 0 or 1,
n is 0 or 1, and
* is a linking point.

6. The compound of claim 1, wherein in Chemical Formula 1, $Ar^3$ is a cyclic group represented by Chemical Formula 2B:

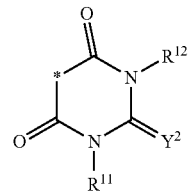

[Chemical Formula 2B]

wherein, in Chemical Formula 2B,
$Y^2$ is each independently O, S, Se, Te, or C($R^a$)(CN) (wherein $R^a$ is hydrogen, a cyano group (—CN), or a C1 to C10 alkyl group),
$R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking point.

7. The compound of claim 1, wherein in Chemical Formula 1, $Ar^3$ is a cyclic group represented by Chemical Formula 2C:

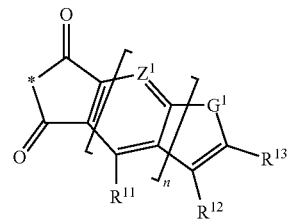

[Chemical Formula 2C]

wherein, in Chemical Formula 2C,
$G^1$ is —O—, —S—, —Se—, —Te—, —Si$R^xR^y$—, or —Ge$R^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group,
$Z^1$ is N or $CR^a$ (wherein $R^a$ is hydrogen or a substituted or unsubstituted C1 to C10 alkyl group),
$R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are each independently present or linked with each other to provide a fused aromatic ring, n is 0 or 1, and

* is a linking point.

8. The compound of claim 1, wherein in Chemical Formula 1, $Ar^3$ is a cyclic group represented by Chemical Formula 2D:

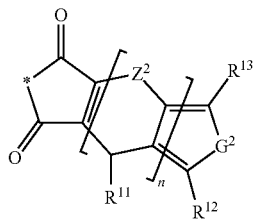

[Chemical Formula 2D]

wherein, in Chemical Formula 2D, $G^2$ is —O—, —S—, —Se—, —Te—, —$SiR^xR^y$—, or —$GeR^zR^w$—, wherein $R^x$, $R^Y$, $R^z$, and $R^w$ are the same or different and are each independently hydrogen, a halogen, a substituted or unsubstituted C1 to C10 alkyl group, or a substituted or unsubstituted C6 to C10 aryl group, $Z^2$ is $NR^a$, $CR^bR^c$, O, S, Se, Te, S(=O), S(=O)$_2$, $SiR^dR^e$, or $GeR^fR^g$ (wherein $R^a$, $R^b$, $R^c$, $R^d$, $R^e$, $R^d$, $R^e$, $R^f$, and $R^g$ are hydrogen or a substituted or unsubstituted C1 to C10 alkyl group), $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

9. The compound of claim 1, wherein at least one of $Ar^1$ and $Ar^2$ includes a heteroatom at position 1, and the heteroatom is nitrogen (N), sulfur (S), or selenium (Se).

10. The compound of claim 1, wherein an electron donor moiety of the N-containing hetero aromatic ring of Chemical Formula 1 is represented by Chemical Formula 4A:

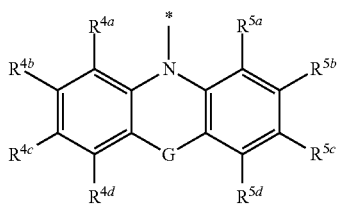

[Chemical Formula 4A]

wherein, in Chemical Formula 4A,

G is the same as in Chemical Formula 1, and $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

11. The compound of claim 1, wherein an electron donor moiety of the N-containing hetero aromatic ring of Chemical Formula 1 is represented by Chemical Formula 4B:

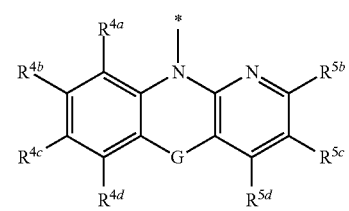

[Chemical Formula 4B]

wherein, in Chemical Formula 4B,

G is the same as in Chemical Formula 1, and $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring, and optionally two adjacent groups of $R^{5b}$ to $R^{5d}$ are linked with each other to provide a 5-membered aromatic ring or a 6-membered aromatic ring.

12. The compound of claim 1, wherein an electron donor moiety of the N-containing hetero aromatic ring of Chemical Formula 1 is represented by Chemical Formula 4C:

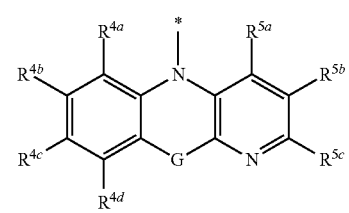

[Chemical Formula 4C]

wherein, in Chemical Formula 4C,

G is the same as in Chemical Formula 1, and $R^{4a}$ to $R^{4d}$ and $R^{5a}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring, and optionally two adjacent groups of $R^{5a}$ to $R^{5c}$ are linked with each other to provide a 5-membered aromatic ring or a 6-membered aromatic ring.

13. The compound of claim 1, wherein an electron donor moiety of the N-containing hetero aromatic ring of Chemical Formula 1 is represented by Chemical Formula 4D:

[Chemical Formula 4D]

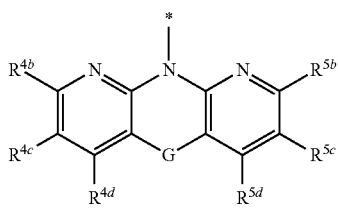

wherein, in Chemical Formula 4D,

G is the same as in Chemical Formula 1, and $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4b}$ to $R^{4d}$ are linked with each other to provide a 5-membered aromatic ring or a 6-membered aromatic ring, and optionally two adjacent groups of $R^{5b}$ to $R^{5d}$ are linked with each other to provide a 5-membered aromatic ring or a 6-membered aromatic ring.

14. The compound of claim 1, wherein an electron donor moiety of the N-containing hetero aromatic ring of Chemical Formula 1 is represented by Chemical Formula 4E:

[Chemical Formula 4E]

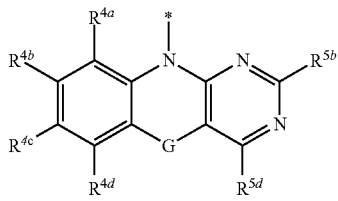

wherein, in Chemical Formula 4D,

G is the same as in Chemical Formula 1, and $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring.

15. The compound of claim 1, wherein an electron donor moiety of the N-containing hetero aromatic ring of Chemical Formula 1 is represented by Chemical Formula 4F:

[Chemical Formula 4F]

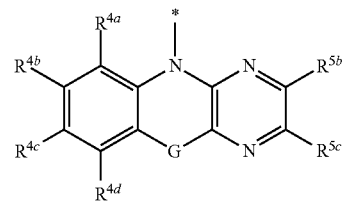

wherein, in Chemical Formula 4F,

G is the same as in Chemical Formula 1, and $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring and optionally two adjacent groups of $R^{5b}$ and $R^{5c}$ are linked with each other to provide a 5-membered aromatic ring or a 6-membered aromatic ring.

16. The compound of claim 1, wherein an electron donor moiety of the N-containing hetero aromatic ring of Chemical Formula 1 is represented by Chemical Formula 4G:

[Chemical Formula 4G]

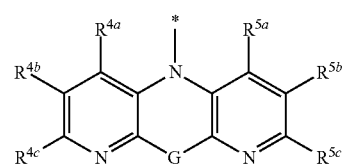

wherein, in Chemical Formula 4G,

G is the same as in Chemical Formula 1, and $R^{4a}$ to $R^{4c}$ and $R^{5a}$ to $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4c}$ are linked with each other to provide a 5-membered aromatic ring or a 6-membered aromatic ring, and optionally two adjacent groups of $R^{5a}$ to $R^{5c}$ are linked with each other to provide a 5-membered aromatic ring or a 6-membered aromatic ring.

17. The compound of claim 1, wherein an electron donor moiety of the N-containing hetero aromatic ring of Chemical Formula 1 is represented by Chemical Formula 4H:

[Chemical Formula 4H]

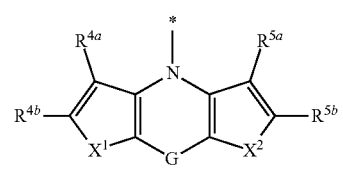

wherein, in Chemical Formula 4H,

G is the same as in Chemical Formula 1, $X^1$ and $X^2$ are each independently O, S, Se, Te or $NR^a$ (wherein $R^a$ is hydrogen, a halogen, a substituted or unsubstituted C1 to C10 alkyl group, or a substituted or unsubstituted C6 to C10 aryl group), $R^{4a}$, $R^{4b}$, $R^{5a}$, and $R^{5b}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ and $R^{4b}$ are linked with each other to provide a 5-membered aromatic ring or a 6-membered aromatic ring and optionally two adjacent groups of $R^{5a}$ and $R^{5b}$ are linked with each other to provide a 5-membered aromatic ring or a 6-membered aromatic ring.

18. The compound of claim 1, wherein the compound has a maximum absorption wavelength ($\lambda_{max}$) in a wavelength region of greater than or equal to about 520 nm and less than or equal to about 600 nm.

19. The compound of claim 1, wherein the compound exhibits a light absorption curve having a full width at half maximum (FWHM) of about 50 nm to about 120 nm, in a thin film state.

20. A photoelectric device, comprising
a first electrode and a second electrode facing each other, and
an active layer between the first electrode and the second electrode,
wherein the active layer includes the compound of claim 1.

21. An image sensor comprising:
the photoelectric device of claim 20.

22. The image sensor of claim 21, wherein
the image sensor includes a semiconductor substrate integrated with a plurality of first photo-sensing devices and a plurality of second photo-sensing devices,
the plurality of first photo-sensing devices are configured to sense light in a blue wavelength region,
the plurality of second photo-sensing devices are configured to sense light in a red wavelength region, and
the photoelectric device is on the semiconductor substrate and configured to selectively sense light in a green wavelength region.

23. The image sensor of claim 22, further comprising:
a color filter layer on the semiconductor substrate, wherein
the color filter layer includes a blue filter that is configured to selectively transmit light in a blue wavelength region and a red filter that is configured to selectively transmit light in a red wavelength region.

24. The image sensor of claim 22, wherein the first photo-sensing device and the second photo-sensing device are stacked in a vertical direction in the semiconductor substrate.

25. The image sensor of claim 21, wherein
the image sensor includes a green photoelectric device, a blue photoelectric device and a red photoelectric device that are stacked,
the blue photoelectric device is configured to selectively absorb light in a blue wavelength region,
the red photoelectric device is configured to selectively absorb light in a red wavelength region,
the green photoelectric device is an organic photoelectric device, and
the green photoelectric device is the photoelectric device.

26. An electronic device comprising:
the image sensor of claim 21.

27. A compound represented by Chemical Formula 1:

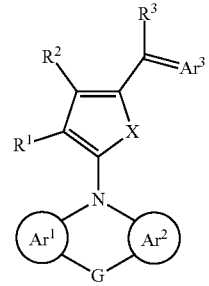

[Chemical Formula 1]

wherein, in Chemical Formula 1, $Ar^1$ and $Ar^2$ are each independently a substituted or unsubstituted C6 to C30 arene group, a substituted or unsubstituted C3 to C30 heteroarene group, or a condensed ring thereof, $Ar^3$ is a substituted or unsubstituted hydrocarbon cyclic group having two carbonyl groups, a substituted or unsubstituted heterocyclic group having two carbonyl groups, or a fused ring thereof, X is Se, Te, or $SiR^aR^b$ (wherein $R^a$ and $R^b$ are each independently hydrogen, a halogen, a substituted or unsubstituted C1 to C10 alkyl group, or a substituted or unsubstituted C6 to C10 aryl group), $R^1$ to $R^3$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein $R^1$ and $R^2$ are each independently present or linked with each other to provide a ring, G is —$SiR^eR^f$—, —$GeR^gR^h$—, —$CR^{cc}R^{dd}$—, —$SiR^{ee}R^{ff}$—, —$GeR^{gg}R^{hh}$—, —$(C(R^{ii})=C(R^{jj}))$—, or $G'(CR^xR^y)_n$, wherein $R^e$, $R^f$, $R^g$, and $R^h$ are each independently hydrogen, a halogen, a substituted or unsubstituted C1 to C10 alkyl group, or a substituted or unsubstituted C6 to C10 aryl group, wherein the pairs of $R^{cc}$ and $R^{dd}$, $R^{ee}$ and $R^{ff}$, $R^{gg}$ and $R^{hh}$, and $R^{ii}$ and $R^{jj}$ are linked with each other to provide a ring, wherein, in $G'(CR^xR^y)_n$, G' is —C—, —Si—, —Ge—, or —C=C—, $R^x$ and $R^y$ are each independently hydrogen, a halogen, a substituted or unsubstituted C1 to C10 alkyl group, or a substituted or unsubstituted C6 to C10 aryl group, and n is an integer of 3 to 8, and wherein an electron donor moiety of the N-containing hetero aromatic ring of Chemical Formula 1 is represented by one of Chemical Formulas 4A to 4H:

[Chemical Formula 4A]

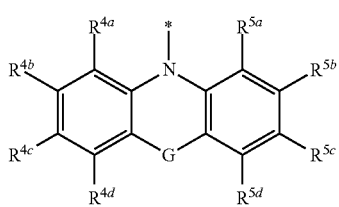

[Chemical Formula 4B]

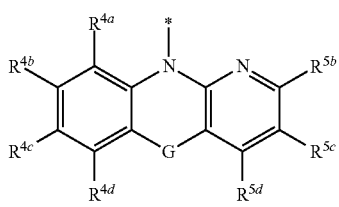

[Chemical Formula 4C]

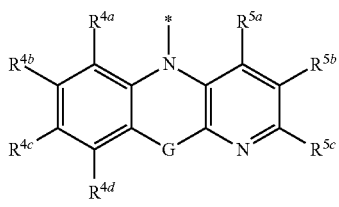

[Chemical Formula 4D]

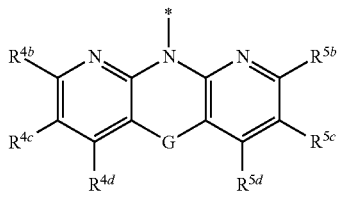

[Chemical Formula 4E]

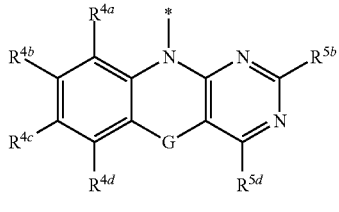

[Chemical Formula 4F]

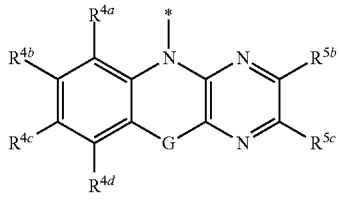

[Chemical Formula 4G]

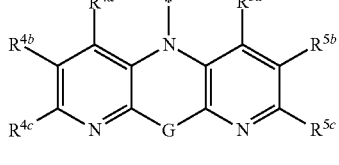

[Chemical Formula 4H]

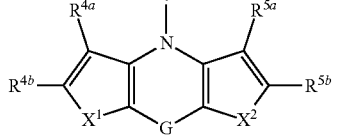

wherein, in Chemical Formulas 4A to 4H,

G is the same as in Chemical Formula 1, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring, and wherein, in Chemical Formula 4H, $X^1$ and $X^2$ are each independently O, S, Se, Te or $NR^a$ (wherein $R^a$ is hydrogen, a halogen, a substituted or unsubstituted C1 to C10 alkyl group, or a substituted or unsubstituted C6 to C10 aryl group).

28. The compound of claim 27, wherein in Chemical Formula 1, $Ar^3$ is a cyclic group represented by one of Chemical Formulas 2A to 2D:

[Chemical Formula 2A]

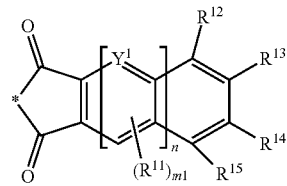

[Chemical Formula 2B]

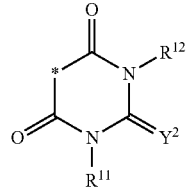

[Chemical Formula 2C]

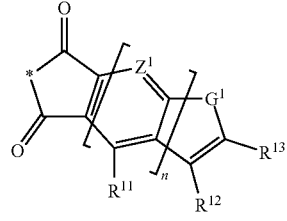

[Chemical Formula 2D]

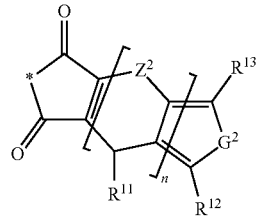

wherein, in Chemical Formulas 2A to 2D,

* is a linking point, wherein, in Chemical Formula 2A, $Y^1$ is N or $CR^a$ (wherein $R^a$ is hydrogen, deuterium, or a substituted or unsubstituted C1 to C10 alkyl group), $R^{11}$, $R^{12}$, $R^{13}$, $R^{14}$, and $R^{15}$ are hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, or a pair of $R^{12}$ and $R^{13}$ or a pair of $R^{14}$ and $R^{15}$ is each independently linked with each other to provide a fused aromatic ring, m1 is 0 or 1, and n is 0 or 1, wherein, in Chemical Formula 2B, $Y^2$ is each independently O, S, Se, Te, or $C(R^a)(CN)$ (wherein $R^a$ is hydrogen, a cyano group (—CN), or a C1 to C10 alkyl group), and $R^{11}$ and $R^{12}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, wherein, in Chemical Formula 2C, $G^1$ is —O—, —S—, —Se—, —Te—, —$SiR^xR^y$—, or —$GeR^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $Z^1$ is N or $CR^a$ (wherein $R^a$ is hydrogen or a substituted or unsubstituted C1 to C10 alkyl group), $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are each independently present or linked with each other to provide a fused aromatic ring, and n is 0 or 1, wherein, in Chemical Formula 2D, $G^2$ is —O—, —S—, —Se—, —Te—, —$SiR^xR^y$—, or —$GeR^zR^w$—, wherein $R^x$, $R^y$, $R^z$, and $R^w$ are the same or different and are each independently hydrogen, a halogen, a substituted or unsubstituted C1 to C10 alkyl group, or a substituted or unsubstituted C6 to C10 aryl group, $Z^2$ is $NR^a$, $CR^bR^c$, O, S, Se, Te, S(=O), S(=O)$_2$, $SiR^dR^e$, or $GeR^fR^g$ (wherein $R^a$, $R^b$, $R^c$, $R^d$, $R^e$, $R^d$, $R^e$, $R^f$, and $R^g$ are hydrogen or a substituted or unsubstituted C1 to C10 alkyl group), $R^{11}$, $R^{12}$, and $R^{13}$ are the same or different and are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and n is 0 or 1.

29. The compound of claim 27, wherein the compound has a maximum absorption wavelength ($\lambda_{max}$) in a wavelength region of greater than or equal to about 520 nm and less than or equal to about 600 nm, and the compound exhibits a light absorption curve having a full width at half maximum (FWHM) of about 50 nm to about 120 nm, in a thin film state.

30. A photoelectric device, comprising a first electrode and a second electrode facing each other, and an active layer between the first electrode and the second electrode, wherein the active layer includes the compound of claim 27.

31. An image sensor comprising:

the photoelectric device of claim 30.

* * * * *